United States Patent

Saito et al.

[11] Patent Number: 5,565,114
[45] Date of Patent: Oct. 15, 1996

[54] METHOD AND DEVICE FOR DETECTING THE END POINT OF PLASMA PROCESS

[75] Inventors: Susumu Saito; Chishio Koshimizu; Kazuo Eguchi, all of Yamanashi-ken, Japan

[73] Assignees: Tokyo Electron Limited, Tokyo; Tokyo Electron Yamanashi Limited, Nirasaki, both of Japan

[21] Appl. No.: 294,396

[22] Filed: Aug. 23, 1994

Related U.S. Application Data

[63] Continuation-in-part of Ser. No. 205,806, Mar. 4, 1994.

[30] Foreign Application Priority Data

| Mar. 4, 1993 | [JP] | Japan | 5-69204 |
| Mar. 4, 1993 | [JP] | Japan | 5-69205 |
| Aug. 23, 1993 | [JP] | Japan | 5-229459 |
| Aug. 31, 1993 | [JP] | Japan | 5-240663 |
| Sep. 28, 1993 | [JP] | Japan | 5-265866 |
| Sep. 28, 1993 | [JP] | Japan | 5-265867 |

[51] Int. Cl.$^6$ ............................. G01N 21/00
[52] U.S. Cl. ............. 216/60; 156/345; 356/72; 356/316
[58] Field of Search ............. 156/626.1, 345; 216/60; 204/192.13, 192.33, 298.32, 298.03; 118/712; 427/10; 356/72, 316

[56] References Cited

U.S. PATENT DOCUMENTS

| 4,289,188 | 9/1981 | Mizutani et al. | 156/626 |
| 4,430,151 | 2/1984 | Tsukada | 156/626 |
| 4,491,499 | 1/1985 | Jerde et al. | 156/626 |
| 4,657,620 | 4/1987 | Davis et al. | 156/626 X |
| 4,948,458 | 8/1990 | Ogle | 156/643.1 |
| 5,045,149 | 9/1991 | Nulty | 156/627 |
| 5,097,430 | 3/1992 | Birang | 156/626 X |
| 5,160,402 | 11/1992 | Cheng | 156/627 |
| 5,226,967 | 7/1993 | Chen et al. | 118/723 I |
| 5,241,245 | 8/1993 | Barnes et al. | 216/22 X |
| 5,290,383 | 3/1994 | Koshimizu | 156/345 |
| 5,320,704 | 6/1994 | Horioka et al. | 156/345 |
| 5,322,590 | 6/1994 | Koshimizu | 156/626.1 |

FOREIGN PATENT DOCUMENTS

| 0379828 | 8/1990 | European Pat. Off. . |
| 4-290428 | 10/1992 | Japan . |
| 5-206072 | 8/1993 | Japan . |

*Primary Examiner*—Thi Dang
*Attorney, Agent, or Firm*—Oblon, Spivak, McClelland, Maier, & Neustadt, P.C.

[57] ABSTRACT

This invention provides an end point detection method including the steps of sequentially detecting, when a process using a plasma is performed for an object to be processed, emission spectra in a specific wavelength band of an active species in the plasma by using a photodetector, calculating sum average values of emission intensities of the emission spectra, calculating the ratio or the difference between the sum average values to obtain a calculated value, and determining a point at which the calculated value exceeds a predetermined reference value as an end point of the process.

14 Claims, 23 Drawing Sheets

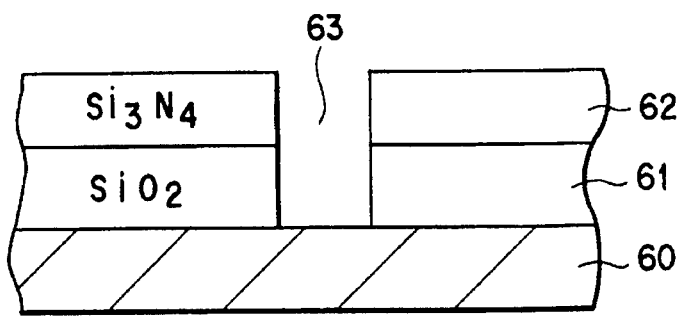
F I G. 12
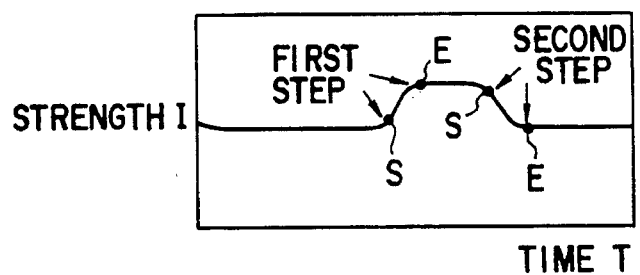
F I G. 13A
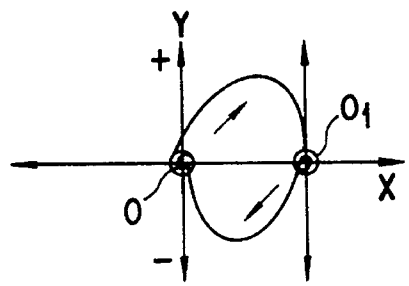
F I G. 13B
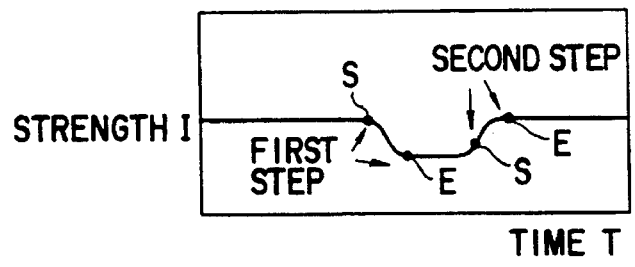
F I G. 13C

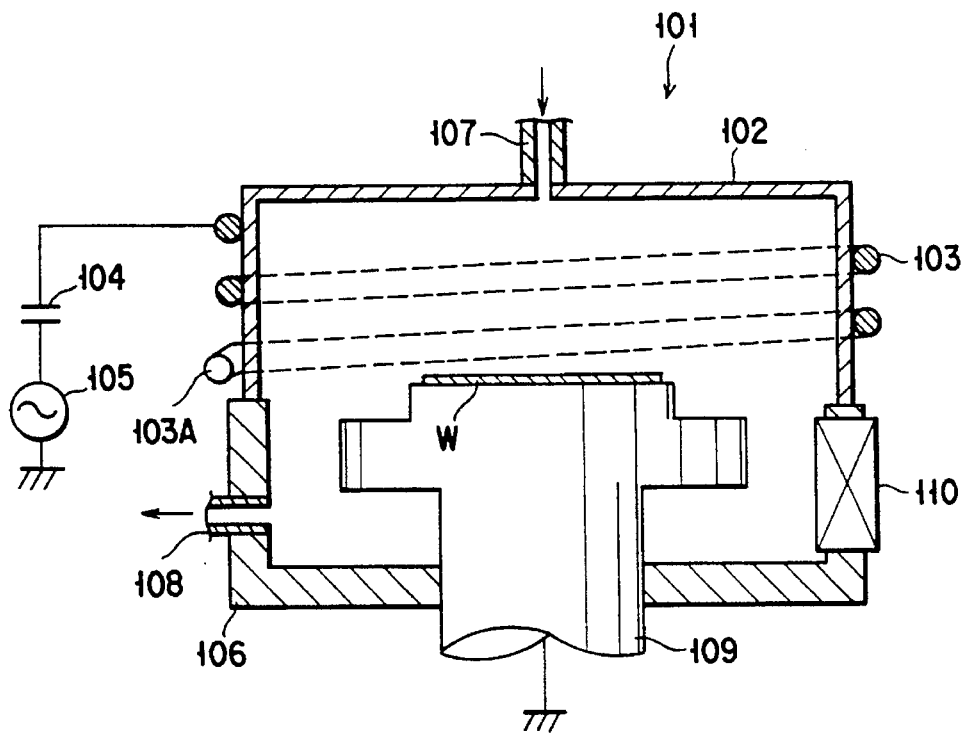
F I G. 21
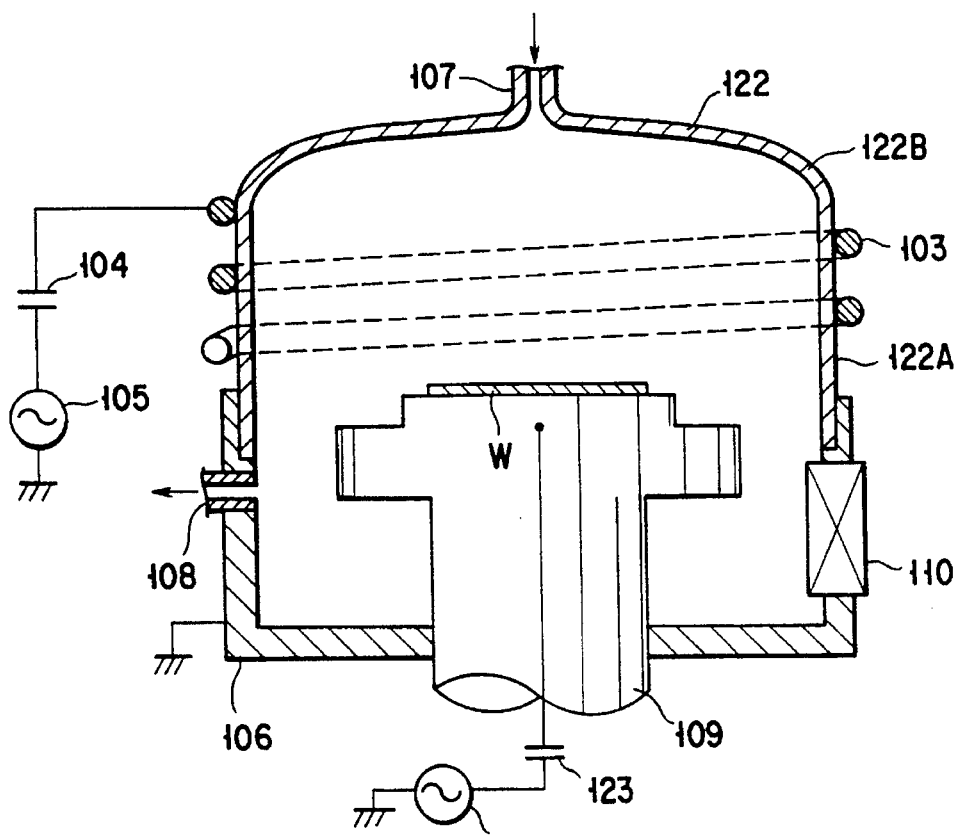
F I G. 22

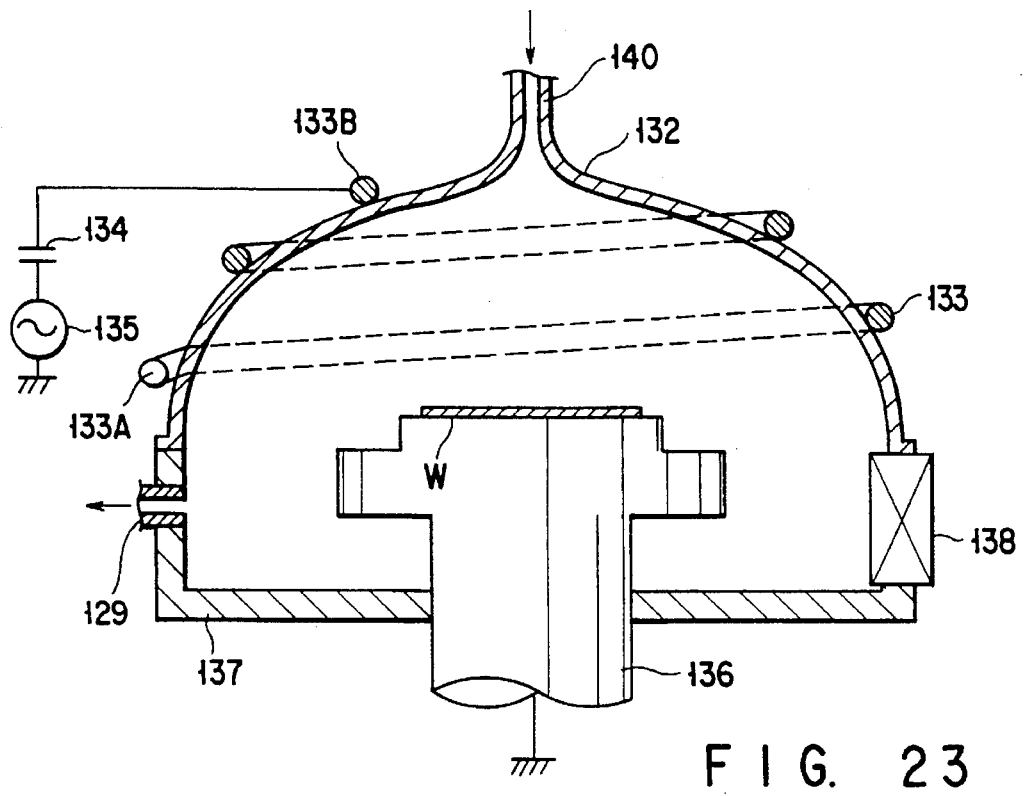
FIG. 23
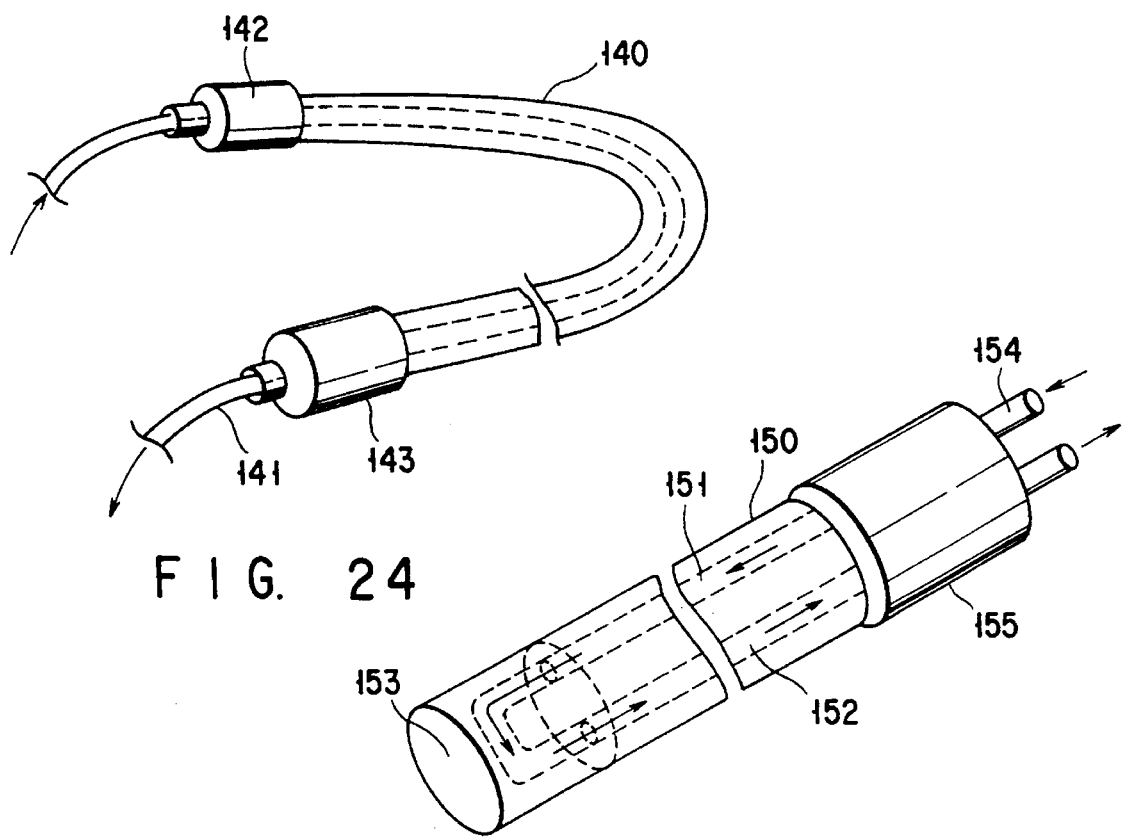
FIG. 24
FIG. 25

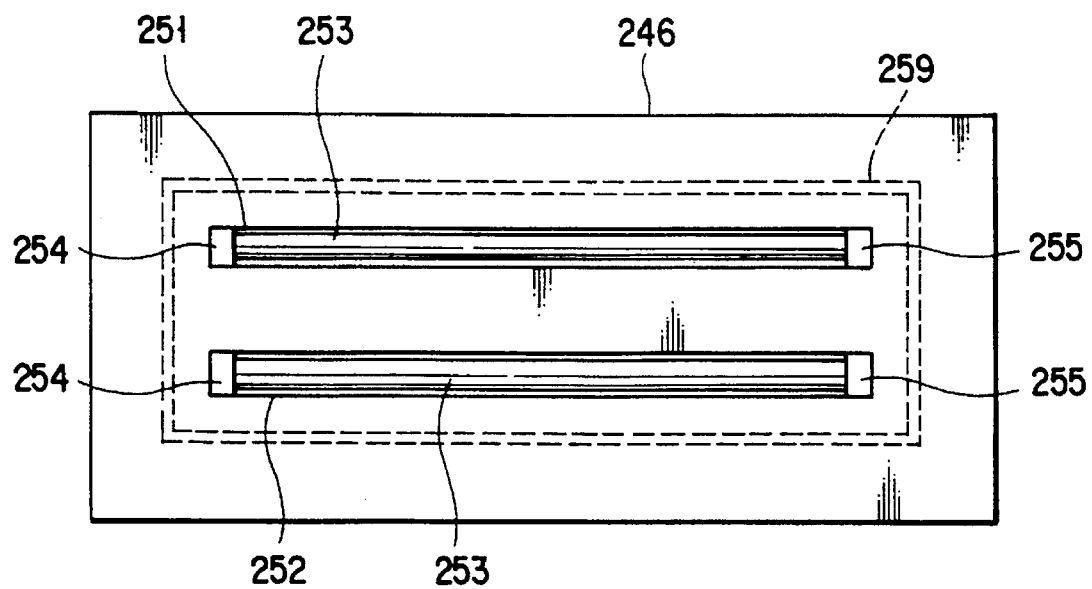
F I G. 29
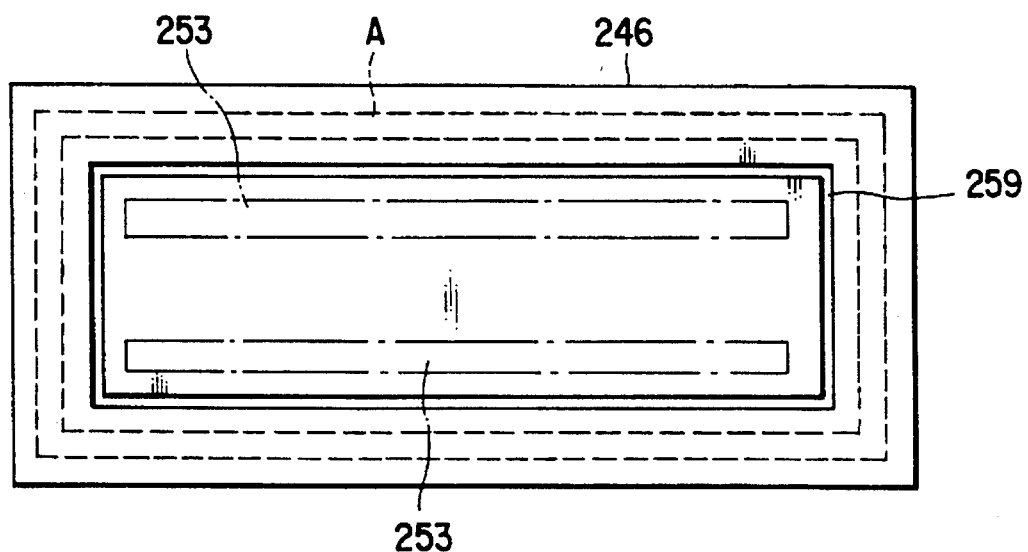
F I G. 30

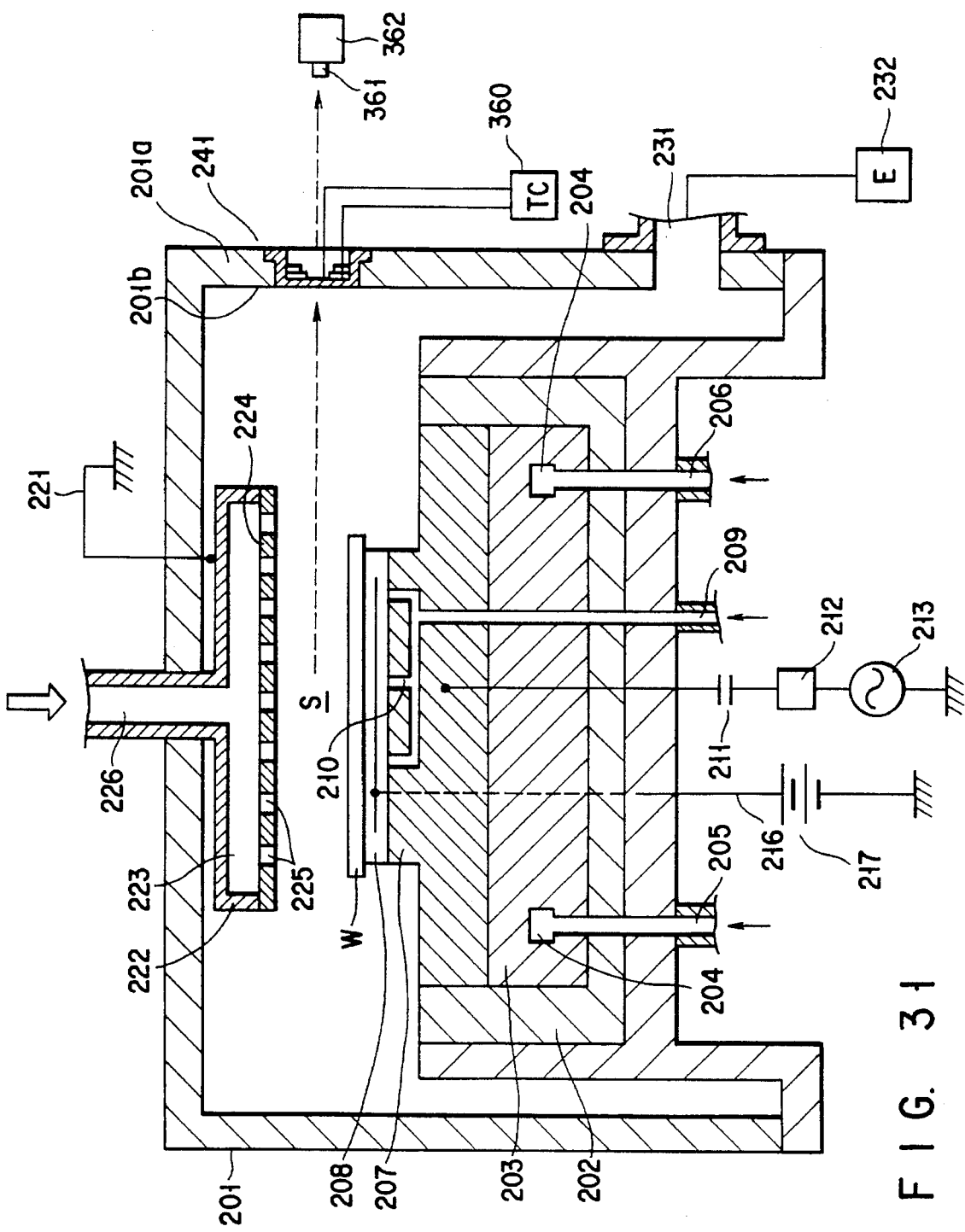
F I G. 31

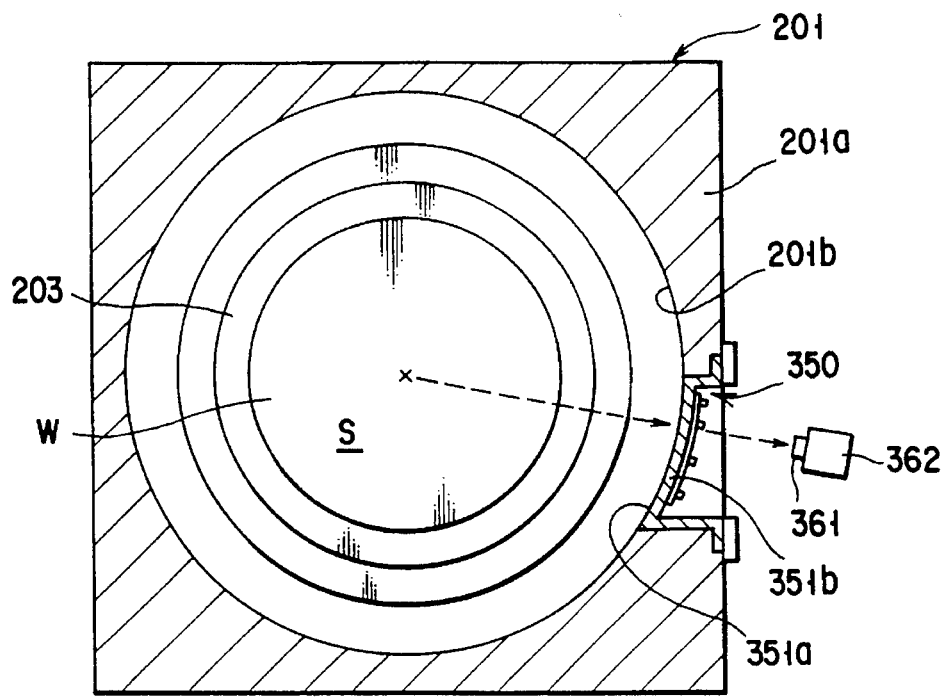
F I G. 36
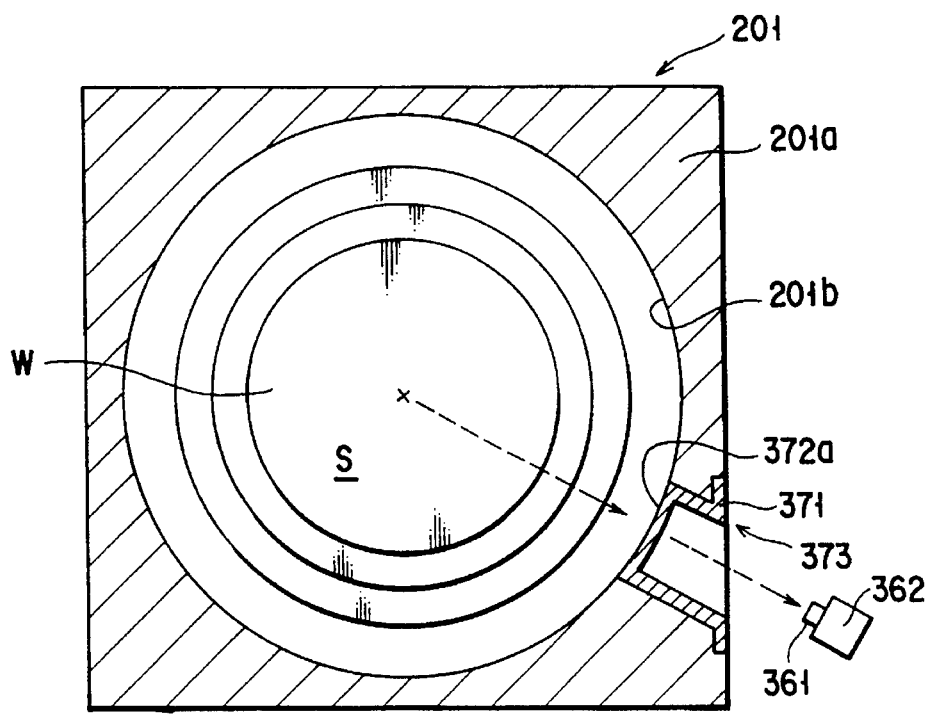
F I G. 37

METHOD AND DEVICE FOR DETECTING THE END POINT OF PLASMA PROCESS

CROSS-REFERENCES TO THE RELATED APPLICATIONS

This application is a continuation-in-part of U.S. patent application Ser. No. 08/205,806 filed on Mar. 4, 1994.

BACKGROUND OF THE INVENTION

1. Field of the Invention

The present invention relates to method and device for detecting the end point of plasma process.

2. Description of the Related Art

The etching apparatus in which plasma is used has been variously incorporated into the course of manufacturing semiconductor devices, and substrates for liquid crystal display devices. It includes upper and lower electrodes arranged parallel to each other and it is intended to etch semiconductor wafers with active species in plasma while discharging between the upper and the lower electrode to make etching gas into plasma. When the semiconductor wafer is being etched, the progress of the etching process is observed and the end point of it is as correctly detected as possible to pattern the wafer as desired.

Conventionally, instrumental analysis methods such as mass spectrometry and spectroscopic analysis are used to detect the end point of etching process. Relatively simple and high sensitive one of them is the spectroscopic analysis. When the spectroscopic analysis is used, a specific active species is selected from radicals, ions and others of etching gas, its decomposed and reacted products and light strengths of the emission spectrum of this active species selected are measured. The active species selected depends upon the kind of etching gas in this case. When etching gas of the fluorocarbon series such as $CF_4$ is used to etch silicon oxide film, spectrum (219 nm, 483.5 nm or others) emitted from the reacted product CO* is measured. When the fluorocarbon series etching gas such as $CF_4$ is used to etch silicon nitride film, spectrum (674 nm or others) emitted from the reacted product N* is measured. The end point of etching process is decided by comparing changing values, which represent the light strength of the above-mentioned active species having a specific wavelength and primary and secondary differential ones of these light strength values, with a threshold previously set.

In the case of the conventional end point detecting methods, however, the active species whose spectrum is measured must be changed depending upon the kind of process used and also the kind of film etched. The threshold, therefore, must also be changed every active species used. Further, when films to be etched belong to the same kind but they are different in thickness, the etching condition under which one of them is etched must be changed from that for the other. This makes it necessary to change the threshold to meet the etching condition changed. In short, the threshold must be changed every etching condition employed, under different etching condition. It needs complexed calculations to set the threshold.

SUMMARY OF THE INVENTION

The present invention is therefore intended to the above-mentioned drawbacks.

Accordingly, the object of the present invention is to provide an end point detecting method and a device for the same, capable of making it unnecessary to change the threshold every process used and every matter processed and also capable of more correctly detecting the end point of plasma process even if the process condition is changed.

This object of the present invention can be achieved by a method of detecting the end point of a plasma process comprising continuously detecting the emission spectrum of an active species in plasma which has a specific wavelength by means of photodetector means when an object is processed with plasma; calculating an average value and dispersed ones from a light strengths of the emission spectrum for a predetermined time period at the initial process stage; calculating their differences relative to the average value from a light strengths after the lapse of the predetermined time period; and comparing values thus arithmetically calculated with the dispersed ones and deciding the end point of the plasma process when the arithmetically-calculated values exceed a predetermined reference value.

The object of the present invention can also be attained by a device for detecting the end point of a plasma process comprising first arithmetical means for calculating an average value and dispersed ones of light strengths, said light strengths being obtained by detecting the emission spectrum of an active species, which has a specific wavelength and which is caused when an object is process with plasma, by photodetector means; second arithmetical means for calculating the differences of said light strengths relative to the average value obtained by the first arithmetical means; comparator means for comparing values obtained by the second arithmetical means with the dispersed ones obtained by the first arithmetical means; and decision means for deciding the time at which values obtained by the comparator means exceed a predetermined reference value to be the end point of the plasma process; wherein the end point of the plasma process is detected on the basis of light strength change of the emission spectrum.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1, FIG. 14, and FIGS. 21 to 23 are views each for explaining major components of a plasma process system including an end point detection apparatus according to the present invention;

FIGS. 8A and 8B are intended to explain the operation of the end point detecting device in FIG. 6, in which FIG. 8A is a graph showing how light strengths and the slope of their waveform change in a case where film same in thickness is etched, and FIG. 8B is X-Y coordinates showing how light strengths and the slope of their waveform in FIG. 8A change;

FIGS. 10A and 10B are intended to explain another operation of the end point detecting device in FIG. 6, in which FIG. 10A is a graph showing how light strengths and the slope of their waveform change when film having some areas different in thickness is etched, and FIG. 10B is X-Y coordinates showing how light strengths and the slope of their waveform in FIG. 10A change;

FIGS. 11A and 11B are intended to explain a further operation of the end point detecting device in FIG. 6, in which FIG. 11A is a graph showing how light strengths and the slope of their waveform change when film same in thickness is etched, and FIG. 11B is X-Y coordinates showing how light strengths and the slope of their waveform in FIG. 11A change;

FIG. 12 is a sectional view showing laminated films etched by the end point detecting method of the present invention;

FIGS. 13A through 13C are intended to explain a still further operation of the end point detecting device in FIG. 6, in which FIG. 13A is a graph showing that the light strength changes like a convex at the time of etching process, FIG. 13B is X-Y coordinates showing how light strengths and the slope of their waveform in FIG. 13A change, and FIG. 13C is a graph showing that the light strength changes like a concave at the time of etching process;

FIGS. 24 and 25 are views each for explaining a loop antenna having a cooling structure applicable to the plasma process system including the end point detection apparatus according to the present invention;

FIGS. 26 and 31 are schematic views each showing a plasma process system to be used in the end point detection method of the present invention;

FIG. 29 is a front view of the transparent member of the plasma process system in FIG. 26;

FIG. 30 is a rear view of the transparent member of the plasma process system in FIG. 26;

FIGS. 36 and 37 are views for explaining the operations of the end point detection method of the present invention.

DETAILED DESCRIPTION OF THE PREFERRED EMBODIMENTS

According to the present invention, emission spectra are detected one after the other by photodetector means, an emission spectrum having a specific wavelength is separated from these emission spectra, and an average value of light strengths of this emission spectrum and dispersed values of them are calculated and stored for a predetermined time period $T_1$ from the start of a plasma process. After the lapse of this predetermined time period $T_1$, the difference of the above-mentioned average value relative to a value representing a light strength then obtained is calculated and it is compared with the dispersed values. When the value thus obtained exceeds a reference value, it is decided that the plasma process is finished. In short, this time tells the end point of the plasma process. An example of the present invention will be described in detail with reference to the accompanying drawings.

EXAMPLE 1

Figure 1:
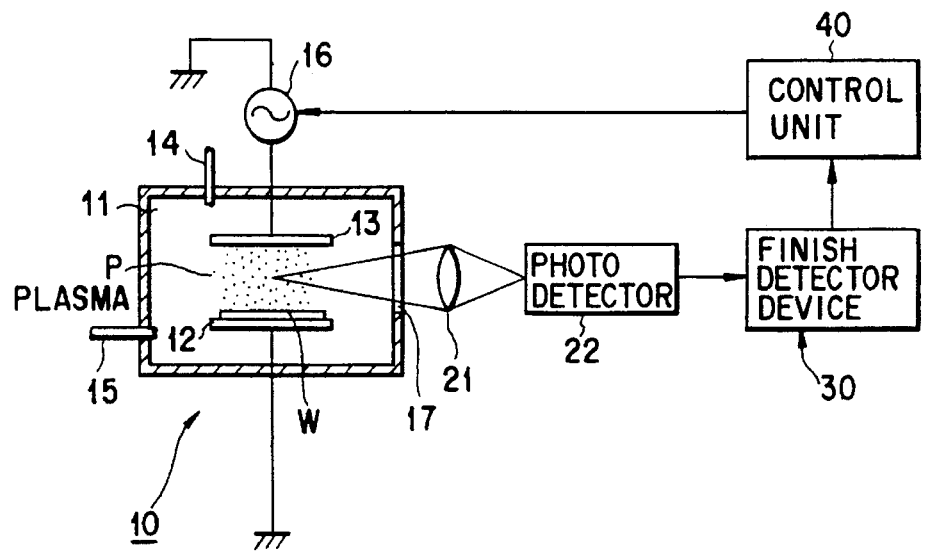

FIG. 1 shows the plasma process apparatus to which an end point detecting device according to the present invention is provided. This plasma process apparatus comprises a process chamber 11 made of conductive material such as aluminium, a lower electrode 12 arranged in the process chamber 11 and serving as a susceptor on which an object such as a semiconductor wafer W to be processed is placed, and an upper electrode 13 arranged above the lower one 12 with an interval between them.

A gas supply pipe 14 is connected to the top of the process chamber 11 to introduce etching gas of the fluorocarbon series such as $CF_4$ into the chamber 11 through it. An exhaust pipe 15 is also connected to a side of the chamber 11 to exhaust gases generated outside the chamber 11 through it. The lower electrode 12 is electrically grounded and it is thus kept to have ground potential. The upper electrode 13 is connected to a high frequency power source 16. High frequency voltage is applied to the upper electrode 13 from the power source 16 to discharge between the upper 13 and the lower electrode 12. The etching gas in the chamber 11 is thus activated to generate plasma P which includes active species such as radicals and ions.

A window 17 made of transparent material such as quartz glass is attached to that side of the process chamber 11 which is opposed to the exhaust-pipe-connected side thereof. The emission spectra of plasma P are passed through the window 17 and analyzed to check the etching process. A lens 21 is arranged outside and behind the window 17 to collect the emission spectra thus passed. A photodetector 22 is further arranged behind the lens 21 to detect and photoelectrically convert the emission spectra thus collected. The photodetector 22 comprises an interference filter or spectroscope, and a photodiode or a photomultiplier, for example. The emission spectrum having a a specific wavelength is separated from the emission spectra by the interference filter or spectroscope and it is photoelectrically converted into signal which denotes its light strength. Responsive to this signal applied from the photodetector 22, the end point detecting device 30 which will be described later detects the end point of the etching process and send control signal to a control unit 40. Responsive to control signal thus applied, the control unit 40 controls the plasma process apparatus 10 to end point the etching process.

The lens 21 can be moved by lens driver means 21a. When the emission spectrum having a specific wavelength is to be detected in a case where film on a semiconductor substrate is to be etched, light reflected by the top surface of film interferes with one reflected by the bottom surface (or interface of film relative to the semiconductor substrate) of film. This makes it impossible to accurately detect the light strength of the emission spectrum. This, however, can be prevented when a focus point of the lens 21 can be moved, as desired, by the lens driver means 21a. The thickness of film changes as etching process advances. It is therefore desirable that the lens 21 is moved to change its focus point as the film thickness reduces.

Figure 2:
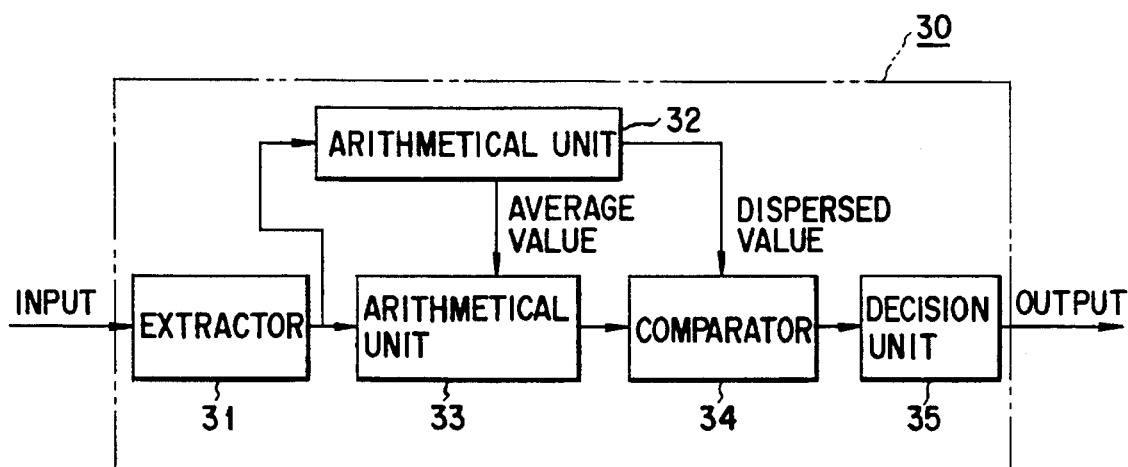
FIG. 2 is a block diagram showing the end point detecting device in FIG. 1.

The end point detecting device 30 according to the present invention will be described with reference to FIGS. 1 through 4. As shown in FIG. 2, it comprises an extractor 31 for extracting elements such as light strength I and linear differential value (or slope) of the waveform from signal or waveform of light strength I applied from the photodetector 22, an arithmetical unit 32 for calculating an average value m and dispersed values $\sigma^2$ from light strengths I (see FIG. 3) extracted one after another by the extractor 31, another arithmetical unit 33 for calculating the difference of average value m applied from the arithmetical unit 32 relative to light strengths I applied from the extractor 31, a comparator 34 for comparing the values of difference applied from the arithmetical unit 33 with dispersed values o2 applied from the arithmetical unit 32, and a decision unit 35 for deciding the end point of etching process when the absolute-value of compared values applied from the comparator 34 exceeds a predetermined reference value. The decision made by the decision unit 35 is applied to a control unit 40, which controls the high frequency power source 16 and others, responsive to signal thus applied, to thereby control etching process.

It will be described how the end point of an etching process is detected by the end point detecting device according to the present invention. The average value m and dispersed ones $\sigma^2$ which represent light strengths I of plasma p for the predetermined time period $T_1$ are calculated at the initial etching stage by the arithmetical unit 32. The amount of etching gas to be used and the irregularity of light strengths I caused by electric noises are thus statistically grasped or checked from these values. After the lapse of the predetermined time period $T_1$, the difference of the average value m relative to the light strength I, which changes as time goes by, is calculated by the arithmetical unit 33. The values of difference are then compared with the dispersed values $\sigma^2$ by the comparator 34. When an absolute-value thus obtained exceeds the reference value, the decision unit 35 decides that the etching process is finished.

The predetermined time period $T_1$ at the initial etching stage is a certain time length optionally set from the start to the end of etching process, and it is not under the control of etching conditions but common to various kinds of etching process. When the average value m and dispersed ones $\sigma^2$ are obtained in this manner from the waveform of light strengths I which change for the predetermined time period $T_1$, the upper and the lower value of light strengths I which change as etching process advances can be checked or grasped at the initial etching stage. When the values of difference obtained between light strengths I and the average value m are compared directly with the dispersed values $\sigma^2$ after the lapse of the predetermined time period $T_1$, the standard deviation o of the dispersed values $\sigma^2$ is used and when the compared value exceeds this deviation or reference value, it is decided that an etching process is finished. In short, average value m and dispersed ones $\sigma^2$ calculated every etching process can be used as the reference value or threshold on which the end point of etching process is decided by the decision unit 35.

Referring to a flow chart in FIG. 4, it will be described how the end point detecting device 30 is operated. A semiconductor wafer W on which silicon oxide film has been formed is seated on the lower electrode 12 in the process chamber 11 which has been decompressed to a range of 0.1 m Torr—several Torr, for example. High frequency voltage is applied from the high frequency power source 16 to the upper electrode 13 and discharged between the upper 13 and the lower electrode 12. Etching gas whose main component is $CF_4$, for example, is supplied into the process chamber 11 through the gas supply pipe 14 and $CF_4$ and others are made plasma to generate active species. When silicon oxide film on the semiconductor wafer W is etched by these active species, $SiF_4$ and CO* (monitor species) are produced. Their emission spectra caused when active species such as CO* return to their ground state pass through the window 17 of the process chamber 11 and come to the photodetector 22 through the lens 21. The photodetector 22 separates the emission spectrum of CO* (483.5 nm) from the plural emission spectra detected, then photoelectrically converts it into electric signal, which represents light strength I, and sends it, as data signal, to the end point detecting device 30.

Figure 4:
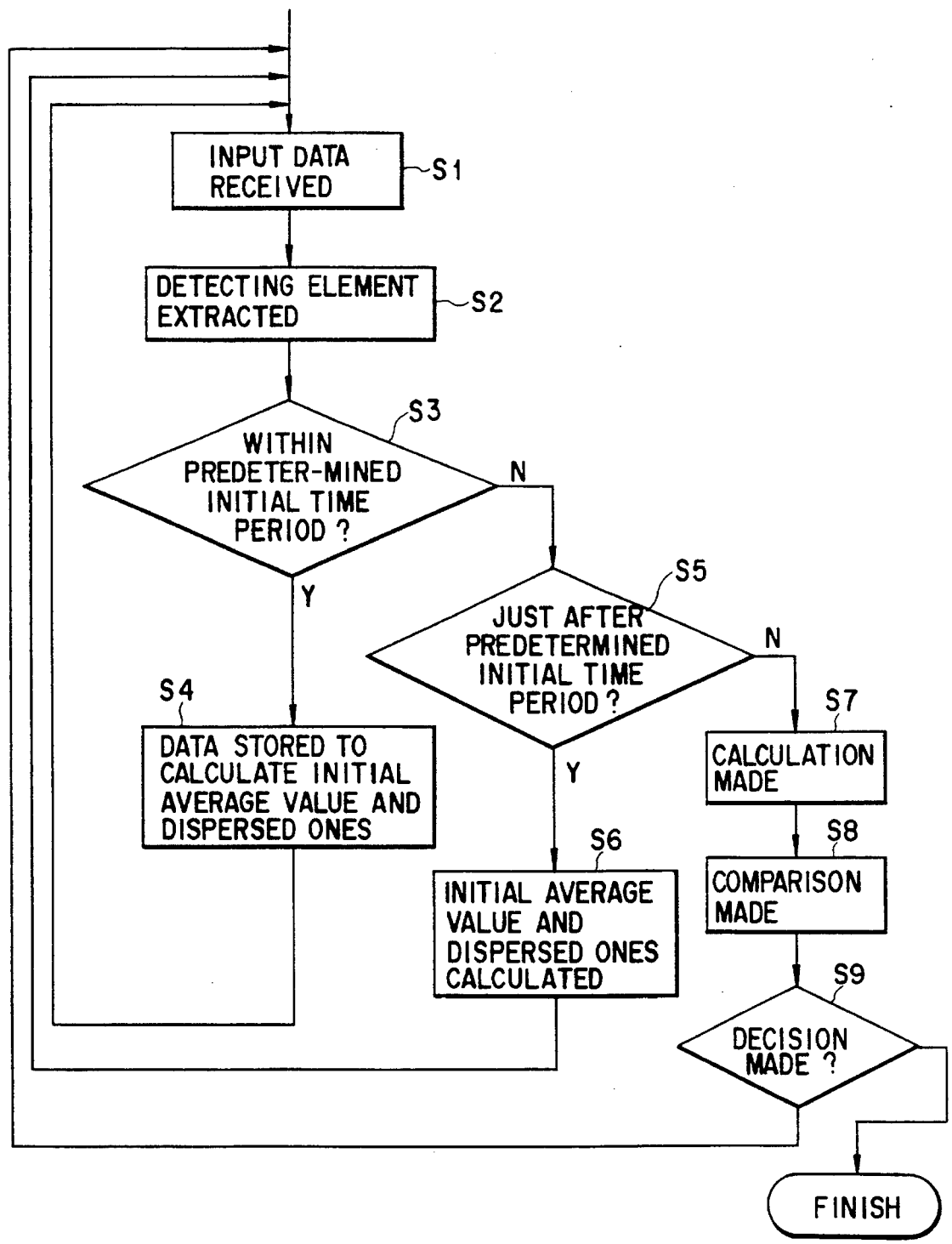
FIG. 4 is a flow chart showing how the end point detecting method according to an embodiment of the present invention is realized by the end point detecting device in FIG. 1.

When the data signal is received by the end point detecting device 30, the following steps are carried out inside the end point detecting device 30, as shown in FIG. 4. The data signal is received as input data by the extractor 31 of the end point detecting device 30 (S1). The extractor 31 extracts those input data which represent light strengths I from the ones received (S2) and confirms whether or not it is within the predetermined initial time period $T_1$ that these input data have been received by the extractor 31 (S3). When the answer is "yes", the extractor 31 sends input data one after another to the arithmetical unit 32, which only stores the input data received (S4). The process then returns to S1 and the above-mentioned steps are repeated to store more and more input data in the arithmetical unit 32. When the answer is "no" at S3, the process advances to S5 and it is confirmed whether or not the predetermined initial time period $T_1$ has passed. When it is confirmed that the predetermined time period $T_1$ has just passed, the average value m and dispersed ones $\sigma^2$ of light strengths I are immediately calculated, on the basis of the input data stored, by the arithmetical unit 32 (S6). The process then returns to S1.

When it is confirmed at S5 that the predetermined time period $T_1$ has passed, signals which represent the average value m and dispersed ones $\sigma^2$ are sent from the arithmetical unit 32 to the arithmetical unit 33 and the comparator 34. The arithmetical unit 33 stores the average value m and calculates the difference of input data received one after another from the extractor 31 relative to the average value m stored (S7). Signals which denote the values of difference are thus sent one after another from the arithmetical unit 33 to the comparator 34. The comparator 34 compares the difference values with the dispersed ones $\sigma^2$ (or standard deviation o in more concrete) already stored (S8) and send results thus obtained to the decision unit 35. Responsive to each of these results, the decision unit 35 decides whether or not the absolute-value of difference exceeds the reference value (S9) and when it does not exceeds the reference value, the process returns to S1 and this decision is repeated. When it is decided at S9 that it exceeds the reference value, the etching process is regarded as coming to its end point and control signal is sent from the decision unit 35 to the control unit 40 to finish the etching process.

Figure 3:
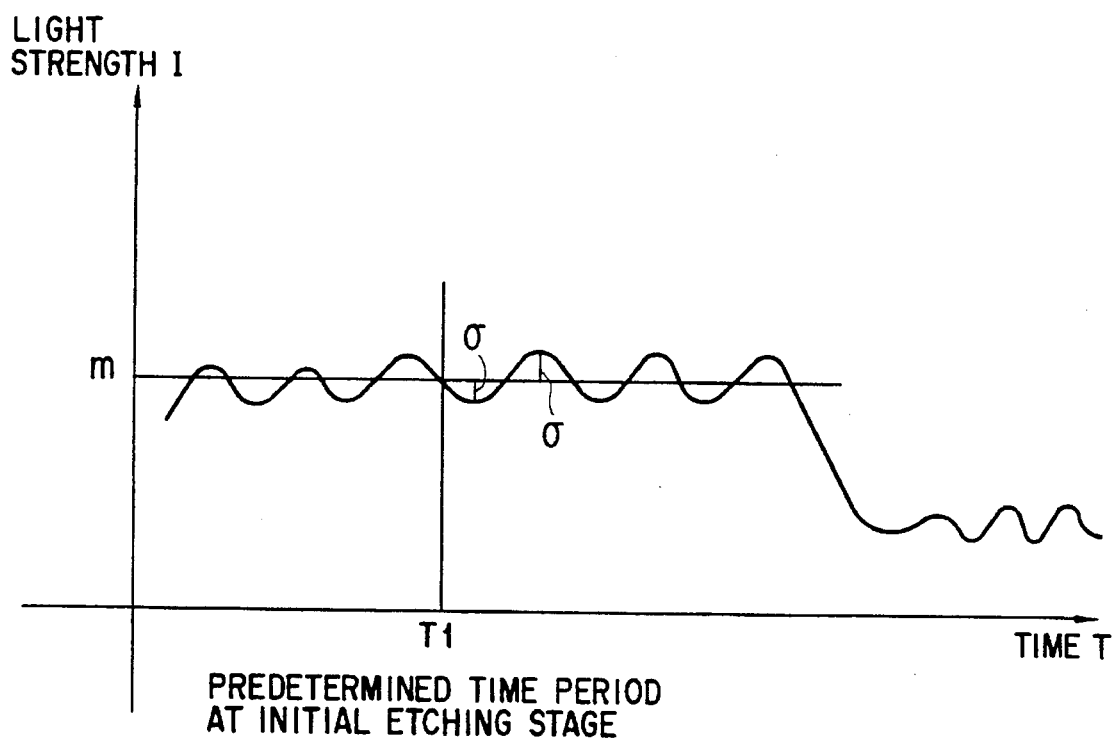
FIG. 3 is a graph intended to explain the operation of the end point detecting device in FIG. 1.

According to the above-described example of the present invention, the arithmetical unit 32 receives data signals, which relate to light strengths I, one after another from the extractor 31 and stores them therein within the predetermined initial time period $T_1$ of etching process. On the basis of these data signals thus stored, it calculates the average value m and dispersed ones $\sigma^2$ of the light strength data. After the lapse of the predetermined initial time period $T_1$, the arithmetical unit 33, the comparator 34 and the decision unit 35 cooperate with one another to decide the end point of etching process on the basis of data signals, or light strengths I, their average value m and dispersed ones $\sigma^2$ received one after another from the extractor 31 and the arithmetical unit 32. Even when etching conditions such as the amount of etching gas supplied are made a little different from the previous ones and the waveform of light strengths I is made unstable by electric noises, as shown in FIG. 3, therefore, the change of light strengths I between the upper and the lower limit at the time of etching process can be clearly distinguished from that at the end point of etching process thanks to electric signals applied from the photodetector 22. This enables the end point of an etching process to be correctly detected to achieve the etching process as desired. It is therefore unnecessary to set a threshold every time etching conditions change. In other words, the present invention enables the end point of an etching process to be correctly and efficiently detected even if etching conditions become different.

In the case of the above-described example, light strengths I of a spectrum caused when activators of plasma P return to their ground state are statistically processed and the end point of etching process is detected on the basis of light strengths I thus statistically processed. However, the present invention is not limited to light strengths. Primary or secondary differential values of a curve which can be drawn while measuring light strengths with the lapse of time may be statistically processed to detect the end point of etching process. Further, the method and device of the present invention are not limited to the purpose of detecting the end point of etching process. They may be applied to those cases such as an ashing apparatus where emission spectra change as the plasma process advances.

EXAMPLE 2

In the conventional methods, the end point of etching process is detected using a detecting element. When the detecting element used changes quite a little. therefore, its change is offset by its forced change caused by the change of etching conditions or by electric noises. In short, its true change cannot be distinguished from its forced change, to thereby make it impossible to detect the end point of etching process.

Figure 5:
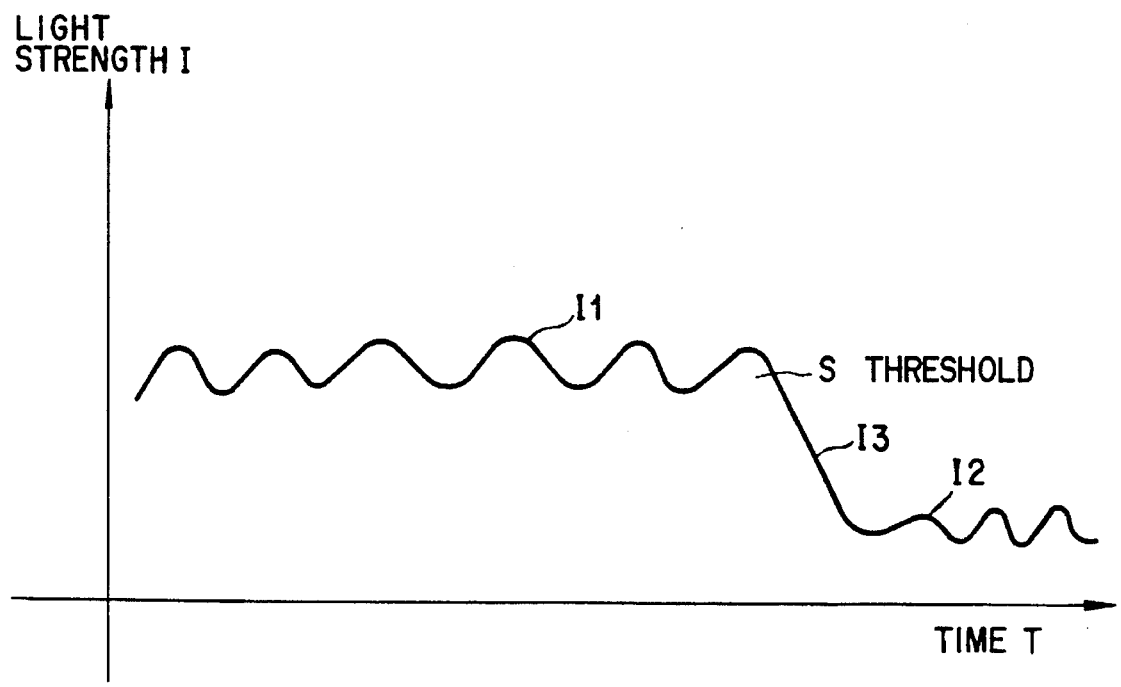
FIG. 5 is a graph showing a light strength waveform of an emission spectrum seen from the start to the end of etching process.

Further, a detecting element such as light strength I is compared, at the time of etching process, with a threshold previously set. In those cases where the end point of etching process changes every etching process applied, the waveform of light strengths changes drawing plural steps, and it has a convex and concave form because of various layers of different films formed on the semiconductor substrate, therefore, end point decision must be repeated every step of it and this makes it more difficult to correctly detect the end point of etching process. When light strength I is selected as the detecting element, for example, it is made unstable by changes in etching conditions such as the flow rate of etching gas, the kind of gas used, pressure and power, as shown by a first waveform $I_1$ at the time of etching process and a second waveform $I_2$ after the end point of etching process in FIG. 5. When that threshold s of a third sloping waveform $I_3$ which denotes the end point of etching process is set adjacent to the start or end of the third waveform $I_3$, therefore it cannot be distinguished from the first or second waveform $I_1$ or $I_2$. Stable end point decision cannot be made, depending upon etching conditions.

According to the present invention there can he provided an end point detecting method and a device for the same, said method and device being capable of correctly detecting the end point of an etching process without any influence of electric noises while secondarily detecting any change in light strength, and also capable of continuously and correctly detecting the end point of each etching process applied to each film layer when film layers on a semiconductor substrate are different from one another in thickness.

Figure 6:
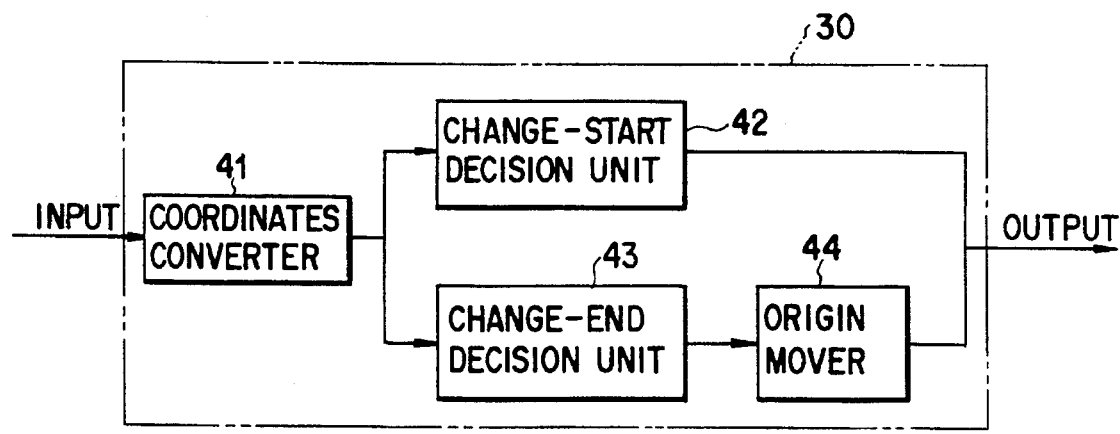
FIG. 6 is a block diagram showing another end point detecting device.
Figure 7:
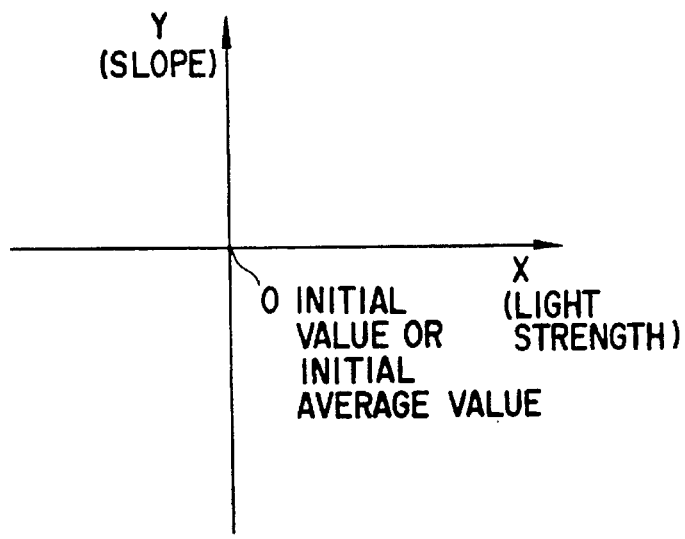
FIG. 7 shows light strengths and their waveform arithmetrically calculated by the end point detecting device in FIG. 6 and plotted in X-Y coordinates.
Figure 8A:
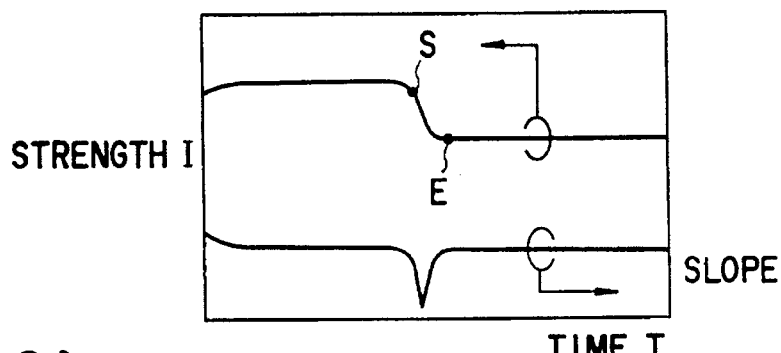
Figure 8B:
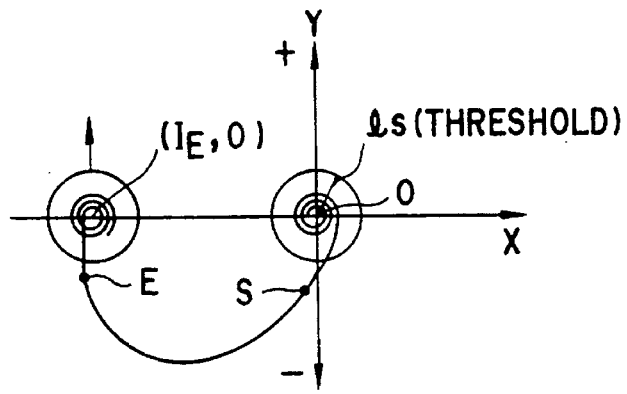
Figure 9:
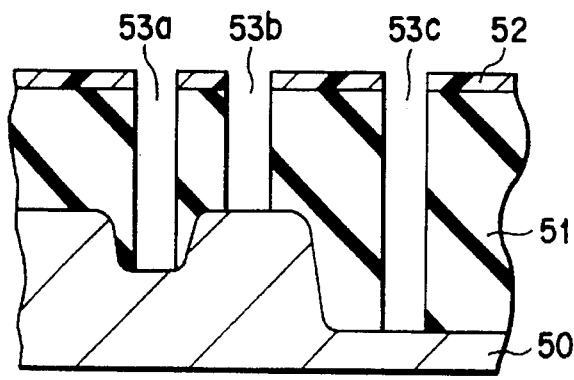
FIG. 9 is a sectional view showing film having some areas different in thickness.
Figure 10A:
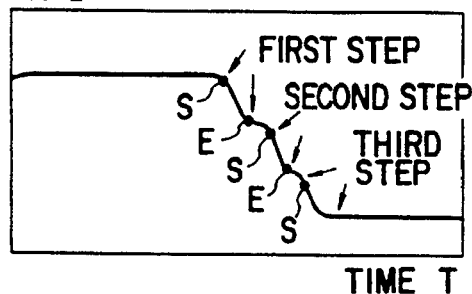
Figure 10B:
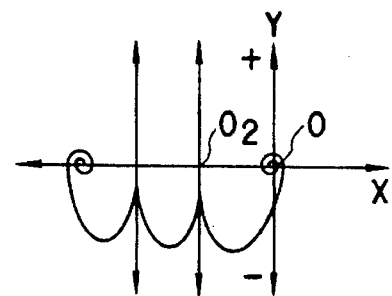

Another end point detecting device 30 according to the present invention will be described referring to FIGS. 6 through 13. As shown in FIG. 6, it comprises an coordinates converter 41 for plotting light strengths I and primary differential values (or slope) of their waveform in X-Y coordinates, as shown in FIG. 7, using input signals applied from the photodetector 22, a change-start decision unit 42 for comparing the distance l of a then-plotted point from the origin O of the X-Y coordinates with a predetermined threshold ls and regarding that point at which the distance l exceeds the threshold ls as a change-start point S (start inflection point) (see FIG. 8B) of the light strength I and also the end point of an etching process, a change-end decision unit 43 for regarding that point at which then-plotted primary differential values which slope after the change-start point S come near to the X axis or that point at which X coordinates values (or light strength) are left unchanged but Y coordinates ones (or slope) come near to the origin O, as shown in FIG. 8B, as a change-end point E (end inflection point) (see FIG. 8A) of the light strength I and also the end point of the etching process, and an origin mover 44 for setting the finish point decided by the change-end decision unit 43 to be a new origin $O_1$ in the X-Y coordinates, as shown in FIGS. 10A and 10B, and moving the origin O to this new origin $O_1$. The threshold ls is determined by the following equation (I):

$$ls = A \times \sqrt{(Sx^2 + Sy^2)} \quad (I)$$

wherein Sx is a dispersed value of X (light strength), Sy is a dispersed value of Y (slope), and A is an arbitrarily constant.

The coordinates converter 41 is intended to convert values of light strength I and slope into x and Y coordinates values, responsive to input signals applied from the photodetector 22, to trace the light strength and the slope in the X-Y coordinates. It is also intended to set the initial values of light strength I and slope or their initial average values for a predetermined initial time period as the origin O of the X-Y coordinates. The predetermined initial time period is a certain time optionally set from the start to the end of etching process. It is a time not depending upon various kinds of etching condition but common to various kinds of etching process. The changestart decision unit 42 serves to receive signal applied from the coordinates converter 41 and recognize then plotted points in the X-Y coordinates. It thus decides the end point of etching process, as described above, and it sends this decision result to the control unit 40 to control the plasma process apparatus 10. The change-end decision unit 43 serves to receive signal applied from the coordinates converter 41 and recognize the change-end point E while comprising the slope of then plotted points (or Y coordinates values) with the threshold (or value as near to the origin O in the Y coordinates axis as possible). It thus decides the end point of etching process, as described above, and it sends this decision result to the origin mover 44. When a layer of film 51 formed on the uneven surface of a substrate 50 is to be etched, while using a layer of resist 51 as a mask, to form recesses 53a–53c each having a different depth in the film layer 51, as shown in FIG. 9, the waveform of light strengths changes drawing a step-like reducing curve or a convex or concave curve, as shown in FIGS. 10A, 13A and 13C, every time the etching of each recess is finished. The origin mover 44 serves to receive signal applied from the change-end decision unit 43 in these cases and move the origin O to a new origin $O_1$ every time the waveform of light strengths changes its curve. When $SiO_2$ and $Si_3N_4$ film layers 61 and 62 formed one upon the other on a semiconductor substrate 60 are etched with etching gas such as a $CH_3+CF_4+Ar+O_2$ gas to form a recess 63 in them, as shown in FIG. 12, the waveform of light strengths I changes drawing a convex curve, as shown in FIG. 13A.

It will be described how the end point detecting method is carried out by the end point detecting device. Emission spectra caused when the semiconductor wafer W is etched with plasma p are detected one after another by the photodetector 22. That one of these emission spectra which has a specific wavelength is selected and the change of its light strength is also used to detect the end point of an etching process in this example. Light strengths I and primary differential values of their waveform are plotted in the X-Y coordinates by the coordinates converter 41, as shown in FIG. 7, and that position at which values then-plotted in the X-Y coordinates begin to remarkably separate from the origin O of the X-Y coordinates is decided to be the end point of the etching process.

More specifically, the origin O of the X-Y coordinates is set using light strengths I (or coordinates values) and their average value for a predetermined time period at the initial etching stage. That position at which the distance l of then-plotted point from the origin O becomes larger than a predetermined threshold ls (see FIG. 8B) can be used as the above-mentioned one at which then-plotted points begin to quickly separate from the origin O. This position is decided to be the change-start point S of light strengths I and also the end point of an etching process by the change-start decision unit 42. At the time of etching process, therefore, light strengths I are not certain but unstable curving up and down, as shown in FIGS. 13A and 13B. As apparent from X and Y coordinates values, therefore, points or values then-plotted in the X-Y coordinates continuously change in a range of the threshold ls, curving like a vortex around the origin O, as shown in FIG. 8B. Just before the end point of an etching process, however, light strength I quickly reduces drawing a slope as shown in FIG. 8A. When X coordinates values (representing the light strength) quickly reduce, values then-plotted in the X-Y coordinates depart from the threshold ls as shown in FIG. 8B. This position is detected and decided to be the change-start point S or the end point of an etching process by the change-start decision unit 42. Then-plotted points which have pressed the change-start point S then trace a downward curve downward to the change-end point E in a minus area of Y and X coordinates values. as shown in FIG. 8A. The value of an integral multiple of the dispersed value $\sigma^2$ is preferable to use as the threshold ls.

When the end point of an etching process is detected at the change-end point E, that point at which then-plotted values curving downward from the X axis come again near to it or must to Y=0 is detected and decided to be the change-end point E or the end point of the etching process by the change-end decision unit 43. The change-end point E may be a point at which then-plotted value is smaller than the dispersed value of the slope. After the change-end point E or end point of the etching process, light strengths I become stable at a lower level, although curving up and down. Then-plotted values or points, therefore, trance a vortex-like curve around a coordinate value ($I_E$, 0).

Figure 11A:
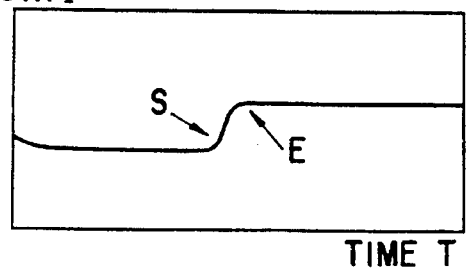
Figure 11B:
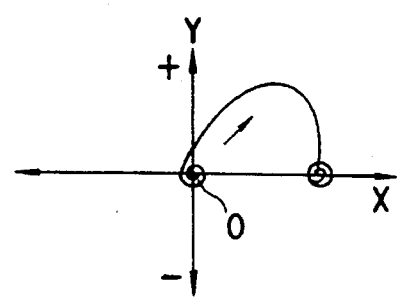

According to the above-described example of the present invention, a spectrum having a specific wavelength is separated from those spectra which are caused from plasma P at the time of etching process is continuously received and the light strength of this spectrum and the slope of its waveform are plotted in the X-Y coordinates. In short, the end point of an etching is detected using secondary changes in the light strength I and the slope. Any change in the light strength I can be thus secondarily detected from the light strength I and the slope of its waveform at the time of the etching process and the end point of the etching process can be correctly detected without any influence of electric noises. When the specific waveform in plasma P of etching gas is viewed, the light strength I becomes stable at the low level because the gas is consumed at the time of the etching process. After the end point of the etching process, however, gas is not consumed. The light strength I, therefore, rises abruptly and changes as shown in FIGS. 11A and 11B. In this case, however, the end point of the etching process can be similarly detected.

When film 51 which is made different in thickness is etched in the same manner, as shown in FIG. 9, the light strength I reduces like a step every time etching is finished relative to each area of film 51 which is different in thickness from the other areas thereof, as shown in FIG. 10A, because the end point of etching process is attained continuously from the thinnest area of film 51 to the thickest area thereof. This can be seen in a case where various kinds of film each having a thickness different from those of the others are etched in the same manner. Every time the end point of etching process is attained continuously from the thinnest film to the thickest one, the light strength I also reduces like a step. In another case where various kinds of film have same thickness but their areas to be etched are different from one another etching is finished from film smallest in area to film largest in area. Therefore, the light strength I also reduces like a step, as shown in FIG. 10A, every time the end point of etching process is attained in each film. In a further case where various kinds of film each having a different etching rate are etched in the same manner, same thing can be said. In short, the light strength I also reduces like a step every time etching is finished successively from film largest in etching rate to film smallest in etching rate.

When first etching is finished in the above cases, the end point of the etching is detected, as described above, by the change-end decision unit 43 and detection signal is sent from the change-end decision unit 43 to the origin mover 44. Responsive to this detection signal applied, the origin mover 44 sets a new origin $O_1$ in the X-Y coordinates by using initial average values of light strengths I and the slope of their waveform for the predetermined initial time period, and it moves the first origin O to the new one $O_1$. The end point of this first etching is thus decided from the change-end point E, as described above, and the same process is repeated to successively move the origin to new ones. When all of etchings are finished, the origin mover 44 send end point signal to the control unit 40 to finish the etching process.

Even in a case where the waveform of light strengths I curves convex as shown in FIG. 13A or concave as shown in FIG. 13C, the origin mover 44 receives signal from the change-end decision unit 43 and moves the origin O to a new one $O_1$ every step of the waveform, as shown in FIG. 13B. Then-plotted points draw upward and downward symmetrical curves along the Y axis in this case.

Even when film to be etched has areas different in thickness, the change-end decision unit 43 and the origin mover 44 can cooperate to continuously and correctly detect the end point of an etching process every area of film. Although signal has been sent from the change-end decision unit 43 to the origin mover 44 in this example, it may be sent from the change-start decision unit 42 to the origin mover 44.

Although the present invention has been applied to the etching process, its method and apparatus can also be applied to a case where emission spectra change as the plasma process advances.

EXAMPLE 3

In conventional plasma process end point detection methods, the peak intensity (peak height) at one particular wavelength is tracked in detecting the emission intensity of the emission spectrum of a selected active species. Therefore, if the emission intensity is low, the S/N (signal-to-noise) ratio decreases to lower the detection sensitivity. This makes it impossible to accurately determine the end point of the plasma process.

In particular, a recent demand for an ultra-high integration degree has required further miniaturization of devices. Accordingly, the size of a region to be subjected to a plasma process, such as etching, has become extremely small. In these cases, the quantity of an active species generated by etching is also very small and is therefore difficult to measure accurately. Generally, the emission intensity of an emission spectrum formed by a plasma reaction fluctuates at any instant due to, e.g., a slight variation in a power supply output, the influence of a massflow controller, a variation in a process pressure, and an increase in a substrate temperature caused by the plasma. Consequently, the S/N ratio further decreases to make it difficult to accurately measure changes in the emission intensity of the emission spectrum of an active species.

In this embodiment, therefore, there is provided a method capable of accurately detecting the end point of a plasma process at a high S/N ratio even if the detection sensitivity is low due to a low emission intensity of an emission spectrum in the plasma process. More specifically, this embodiment provides an end point detection method comprising the steps of sequentially detecting, when a process using a plasma is performed for an object to be processed, the emission spectrum of an active species in a specific wavelength band in the plasma by using photodetecting means, calculating the sum average value of the emission intensity of the emission spectrum within a predetermined initial period of the process, calculating the ratio or the difference between the sum average value and the emission intensity to obtain a calculated value when the predetermined initial period elapses, and determining a point at which the calculated value exceeds a predetermined reference value as the end point of the process.

Since the emission spectrum of an active species is detected over a wavelength range having a certain fixed width, the detection can be performed for a large quantity of light as a whole even if the quantity of light at each individual wavelength is small. For this reason, even if the emission intensity of an emission spectrum is low or the sensitivity of a photodetector is low, the end point of a plasma process can be detected at a high S/N ratio and a high accuracy.

In addition, in this embodiment, it is also possible to detect the end point of a plasma process by detecting the peak value of the emission intensity of at least one active species and the sum average value of the emission intensity of the emission spectrum of at least one active species in a specific wavelength band, and calculating the ratio or the difference between the peak value of the emission intensity and the sum average value. In this method, while an active species which is easy to detect, i.e., which has a high peak value of an emission intensity is monitored, the emission spectrum of an active species, which is difficult to detect because of a low emission intensity but is important in the plasma process end point detection, is monitored over a wavelength range with a certain fixed width. Therefore, the S/N ratio can be increased by properly selecting an object to be monitored in accordance with the plasma process conditions. Consequently, the end point detection for a plasma process can be performed with a high accuracy.

In this embodiment, it is preferable that the specific wavelength band of an active species or the peak value of the emission intensity of an active species be selected from a range within which it appears strongly relative to the peak values of the emission intensities of other active species. As a consequence, the wavelength band or the peak value of the emission intensity of an active species to be monitored is chosen from a range within which it appears strongly relative to the peak values of the emission intensities of other active species, i.e., from an emission spectral range within which the influence of the emission of other active species is negligible. This allows even a photodetector with a low sensitivity to readily perform detections. In addition, the S/N ratio can be further increased.

It is also preferable to choose an active species of a process gas, as one active species whose sum average value of the emission intensity or peak value of the emission intensity is to be detected, and a reaction product of a plasma process, as the other active species whose sum average value of the emission intensity or peak value of the emission intensity is to be detected. In this case of etching an $SiO_2$ film, a process gas active species, e.g., a CF-based gas such as $CHF_3$ is no longer used when a plasma process is ended, and so the amount of the gas relatively increases. Accordingly, the emission intensity of the emission spectrum also increases. On the other hand, a reaction product, e.g., CO is no longer produced when a plasma process is ended, and so the amount of the reaction product relatively decreases. Accordingly, the emission intensity of the emission spectrum also decreases. In this fashion, the end point of a plasma process is detected on the basis of at least two active species showing different changes at the end of the plasma process. This permits easy determination at a higher accuracy.

Furthermore, in the end point detection method of this embodiment, it is preferable that the peak value of the emission intensity or the wavelength band of an active species to be monitored be selected from a range except for the peak value of the emission intensity of silicon (Si). For example, the peak value of the emission intensity or the wavelength band, e.g., a wavelength band of 255 to 287 nm of an active species to be monitored is selected from a range except for a wavelength band in which the peak value of the emission intensity of silicon as the underlying material of a silicon oxide film appears, e.g., a wavelength band of 243 to 252 nm or a wavelength of 288 nm. This makes it possible to ignore noise resulting from the emission spectrum of silicon, and as a consequence the end point of a plasma process can be detected with a higher S/N ratio.

Also, it is preferable to choose the peak value of the emission intensity of carbon monoxide (CO) as the peak value of the emission intensity of an active species to be monitored. This is preferred particularly in etching a silicon oxide film by using a CF-based process gas. In this case, a change in the peak value of the emission intensity of carbon monoxide (CO) is monitored as one reference. The amount of carbon monoxide (CO) as a reaction product of a silicon oxide film and a CF-based gas decreases abruptly when etching is ended. When the amount of carbon monoxide (CO) decreases abruptly, its emission intensity also decreases abruptly. The result is an easy detection of the end point.

Figure 14:
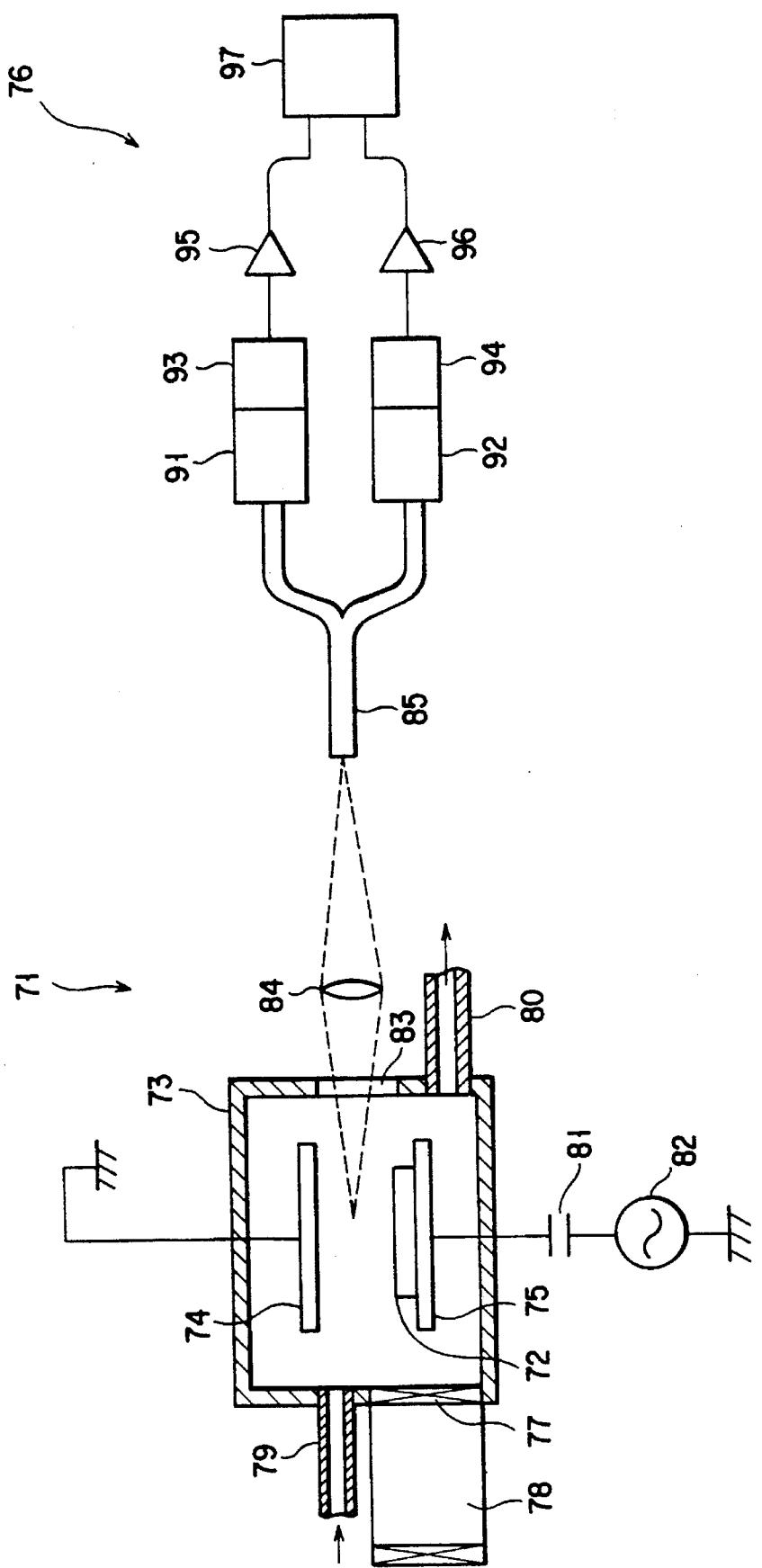

FIG. 14 is a schematic view showing a plasma etching system 71 to which the end point detection method of the present invention is applied. This etching system 71 comprises an airtightly constructed process chamber 73 adjustable to a desired reduced-pressure atmosphere, a pair of opposing upper and lower electrodes 74 and 75 arranged in this process chamber 71, and a controller 76 for monitoring emission spectra in the process chamber 73. An object to be processed, e.g., a semiconductor wafer 72 is fixed on the lower electrode 75 by a fixing means such as an electrostatic chuck. A silicon oxide film formed on the wafer can be selectively etched with a process gas.

The process chamber 73 is coupled with a cassette chamber (not shown) via a gate valve 77 and, if necessary, a load-lock chamber 78. In performing a process, the object 72 can be transferred into or out from the process chamber 73 by a transfer mechanism (not shown) by opening the valve 77. The process chamber 73 is also connected to a gas inlet pipe 79 and an exhaust pipe 80. The gas inlet pipe 79 is for supplying an etching gas, e.g., a CF-based gas such as $CHF_3$ gas, and, if necessary, an inert gas, e.g., argon gas or helium gas. The exhaust pipe 80 is for exhausting, e.g., an excess gas or a reaction product gas. With these pipes 79 and 80, the process chamber 73 can be held in a predetermined reduced-pressure atmosphere at, e.g., 200 mTorr.

The upper and lower electrodes 74 and 75 constitute parallel plate electrodes. That is, the upper electrode 74 is grounded, and the lower electrode 75 is connected to an RF power supply 82 via a matching capacitor 81. With this arrangement, an RF voltage can be applied between the two electrodes. Also, as described above, the object 72 to be processed can be fixed on the lower electrode 75 by using, e.g., an electrostatic chuck.

A window 83 consisting of quartz or the like is also formed in the side wall of the process chamber 73 to transmit the emission of a plasma generated between the upper and lower electrodes 74 and 75 to the outside. In the vicinity of this window 83, a lens 84 for condensing the light transmitted through the window 83 is arranged. The light condensed by the lens 84 is split into two light components through optical fibers 85 and supplied to the controller 76. The window 83, the lens 84, and the optical fibers 85 constitute a photodetecting means. With the use of this photodetecting means, it is possible to detect the emission of short wavelengths up to near 200 nm.

The controller 76 comprises spectroscopes 91 and 92, photoelectric converters 93 and 94, amplifiers 95 and 96, and a determination unit 97. The spectroscopes 91 and 92 obtain the spectra within predetermined ranges of the transmitted light components. The photoelectric converters 93 and 94 convert the light components at the specific wavelengths obtained by the spectroscopes 91 and 92, respectively, into electrical signals. The amplifiers 95 and 96 amplify the electrical signals from the photoelectric converters 93 and 94, respectively. The determination unit 97 executes predetermined calculations for the electrical signals corresponding to the light components at the particular wavelengths and determines the end point of etching from the calculation results.

If a CF-based gas such as $CF_3$ gas is to be used as an etching gas, it is possible to monitor light having a wavelength band ranging from 240 to 350 nm, preferably 240 to 280 nm, and more preferably 255 to 287 nm by using one pair of the spectroscope 91 and the photoelectric converter 93. By selecting the range of light to be monitored from these wavelength bands, it is possible to avoid confusion of the emission spectrum of silicon having peak values of the emission intensity at 243 to 252 nm and at 288 nm with the emission spectrum of a desired process gas and vice versa.

In the end point detection method of this embodiment as discussed above, light in a wavelength band having a certain width is monitored, and the end point of a plasma process is detected by calculating the sum average value of the light in this wavelength band. This allows the use of inexpensive interference filters with a relatively low resolving power which have not been used in conventional methods. In particular, photoelectric conversion can be effected with an inexpensive silicon photodiode by using an interference filter whose half-width is set at 10 to 20 nm by setting the transmission center wavelength in almost the middle of 240 to 280 nm, preferably 255 to 287 nm.

On the other hand, if a reaction product gas, e.g., a reaction product of carbon monoxide is expected to be produced, the other pair of the spectroscope 92 and the photoelectric converter 94 monitor light components in a wavelength band ranging between, e.g., 210 and 236 nm, and the end point of the plasma process is determined by calculating the sum average value of these light components. In this case, it is possible to monitor a specific wavelength selected from the above wavelength band range, e.g., a wavelength of any of 219.0 nm, 230.0 nm, 211.2 nm, 232.5 nm, and 224 to 229 nm. The end point of the plasma process can be determined directly on the basis of the value of an emission intensity at that wavelength.

Figure 15:
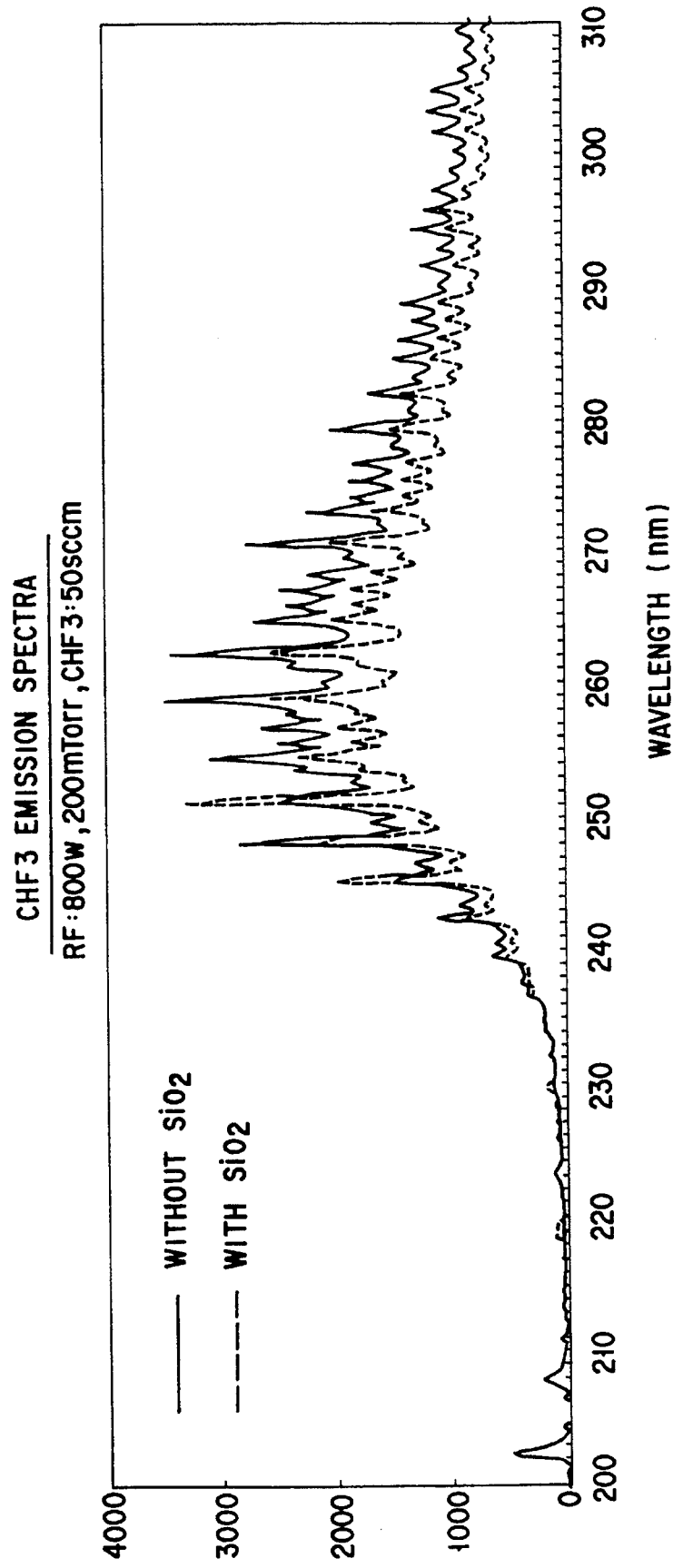
FIG. 15 is a graph showing the emission intensity distributions of emission spectra in a wavelength band of 200 to 310 nm when etching was performed on a silicon oxide film by using $CHF_3$ gas at a process pressure of 200 mTorr.
Figure 16:
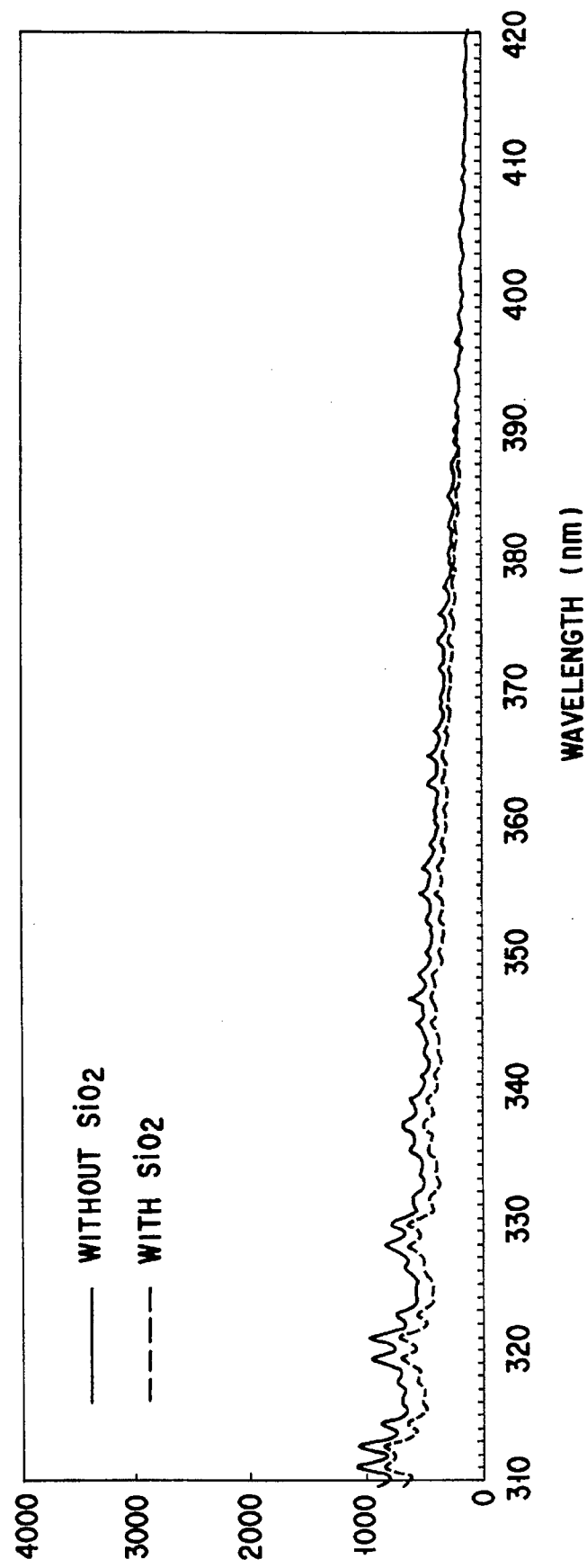
FIG. 16 is a graph showing the emission intensity distributions of emission spectra in a wavelength band of 310 to 420 nm when etching was performed on a silicon oxide film by using $CHF_3$ gas at a process pressure of 200 mTorr.

FIGS. 15 and 16 show emission spectra in a wavelength band of 200 to 400 nm when plasma etching was performed on a silicon oxide film by using $CHF_3$ gas under the conditions of an RF power of 800 W, a process pressure of 200 mTorr, and a $CHF_3$ gas flow rate of 50 sccm. In each of FIGS. 15 and 16, the thick line indicates a wafer on which no silicon oxide film was formed, and the thin line indicates a wafer on the entire surface of which a silicon oxide film was formed.

As can be seen from FIGS. 15 and 16, by monitoring a wavelength band with a certain width by selecting light having a wavelength band of 240 to 350 nm, preferably 240 to 280 nm, and more preferably 255 to 287 nm, a high-accuracy monitoring is possible even if the light intensity of the peak value of each wavelength is low. In particular, by selecting a wavelength band within the above range, a variation in the emission spectrum of a process gas can be monitored without being influenced by a variation in the emission spectrum of silicon having peak values of an emission intensity at 243 to 252 nm and at 288 nm.

Figure 17:
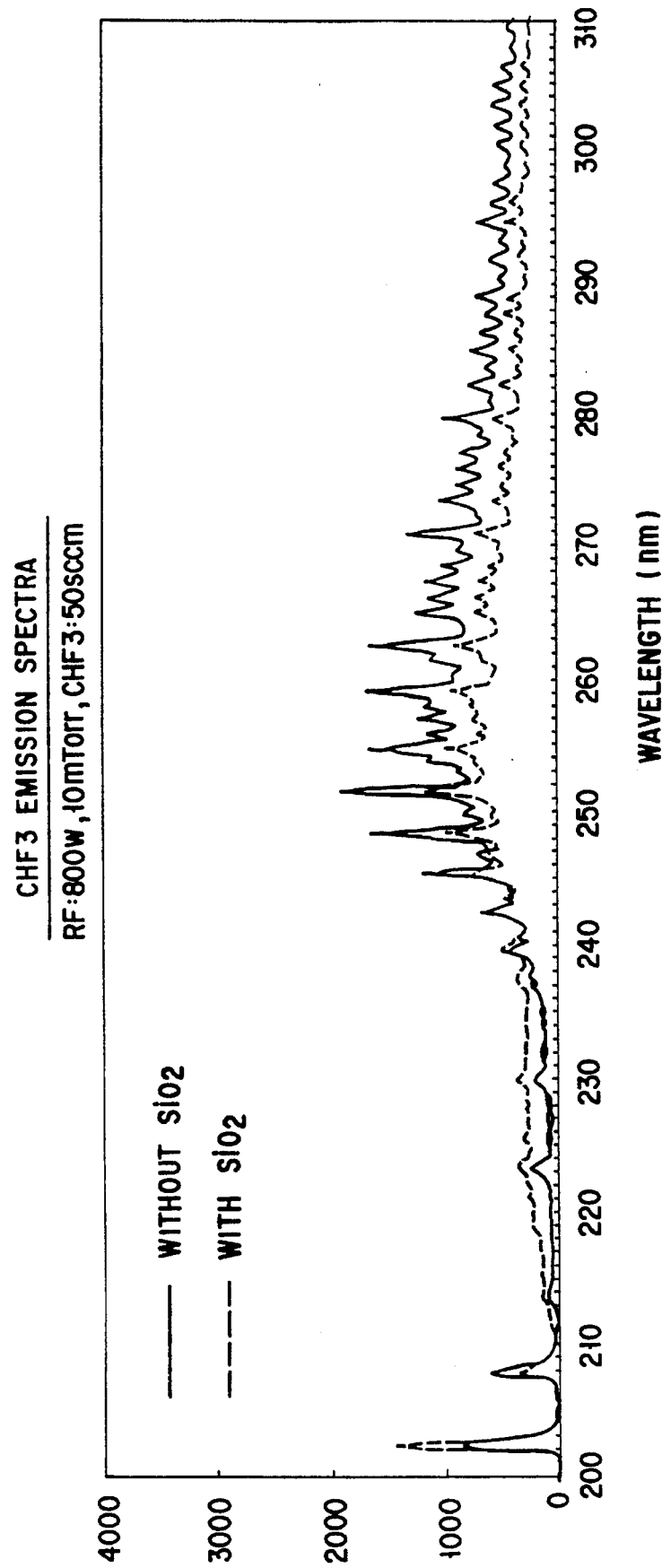
FIG. 17 is a graph showing the emission intensity distributions of emission spectra in a wavelength band of 200 to 310 nm when etching was performed on a silicon oxide film by using $CHF_3$ gas at a process pressure of 10 mTorr.
Figure 18:
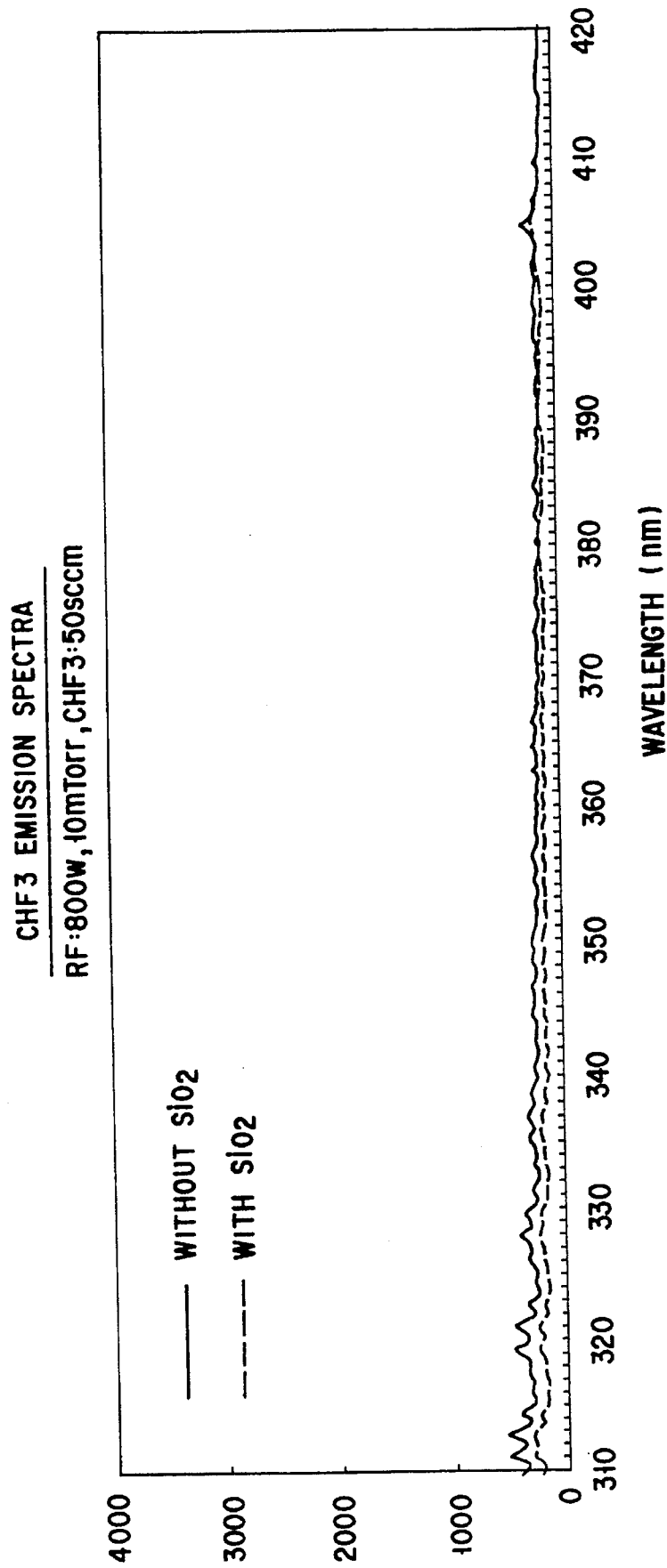
FIG. 18 is a graph showing the emission intensity distributions of emission spectra in a wavelength band of 310 to 420 nm when etching was performed on a silicon oxide film by using $CHF_3$ gas at a process pressure of 10 mTorr.

FIGS. 17 and 18 show emission spectra in a wavelength band of 200 to 400 nm when plasma etching was performed on a silicon oxide film by using $CHF_3$ gas under the conditions of an RF power of 800 W, a process pressure of 10 mTorr, and a $CHF_3$ gas flow rate of 50 sccm. In each of FIGS. 17 and 18, as in FIGS. 15 and 16, the thick line indicates a wafer on which no silicon oxide film was formed, and the thin line indicates a wafer on the entire surface of which a silicon oxide film was formed.

As can be better understood by comparing the etching process at a process pressure of 200 mTorr illustrated in FIGS. 15 and 16 with the etching process at a process pressure of 10 mTorr illustrated in FIGS. 17 and 18, the emission intensity of the emission spectrum of $CHF_3$ gas is low in low-pressure processes which have attracted attention in recent years. If the emission intensity is low as in these instances, it is difficult for a low-sensitivity photodetector to detect the corresponding emission spectrum. In this embodiment, however, emission spectra in a wavelength band of, e.g., 240 to 280 nm are monitored. Therefore, even if the emission intensity of the peak wavelength of each emission spectrum is low, an emission intensity to a certain degree can be obtained as a whole. For this reason, high-accuracy measurements can be performed by calculating the sum average value of these emission intensities. This makes an accurate determination of the end point of a plasma process feasible.

A plasma etching method performed on the basis of this embodiment is described below. First, the object 72 to be processed, e.g., a semiconductor wafer is transferred from the load-lock chamber 78 by a transfer mechanism (not shown) and placed on the lower electrode 75 in the process chamber 73. A mask having a predetermined pattern is already formed on a silicon oxide film of this semiconductor wafer by a regular photolithography process. Subsequently, the gate valve 77 is closed, and the process chamber 73 is evacuated to a predetermined vacuum degree, e.g., 200 mTorr through the exhaust pipe 80. Thereafter, a CF-based gas, e.g., $CHF_3$ gas is supplied as an etching gas at a predetermined flow rate from the gas inlet pipe 79 to keep a predetermined gas pressure. Additionally, an RF power at a predetermined frequency, e.g., 13.56 MHz and a predetermined power, e.g., several hundred watts is applied between the upper and lower electrodes 74 and 75. Consequently, a plasma is generated, and the silicon oxide film on the surface of the object 72 is etched with this plasma.

The CF-based gas, e.g., $CHF_3$ gas supplied into the process chamber 73 dissociates in the plasma to produce various active species such as $CF_2$. These active species react with the silicon oxide film to allow the etching to proceed. By this etching, reaction products such as $SiF_x$, carbon monoxide, and a $CO^+$ ion are formed. Carbon monoxide and a $CO^+$ ion, of these reaction products, and $CHF_3$ gas as the etching gas emit light with their respective specific emission spectra. Therefore, the light components emitted by these substances are detected. The light components emitted in this manner are condensed by the lens 84 through the quartz window 83 of the process chamber 73 and guided to the controller 76 through the optical fibers 85. The light components guided to the controller 76 are then processed and displayed as spectra by the spectroscopes 91 and 92. These spectra are transmitted to the photoelectric converters 93 and 94 as emission spectra at a specific wavelength or as emission spectra contained in a particular wavelength band.

The emission spectrum obtained in this manner is the result of synthesis of the emission spectra of the reaction products and the process gas. Therefore, at a certain wavelength or in a certain wavelength band, the emission intensity of an active species to be detected is considerably higher than the emission intensities of other active species in some cases. In these cases, if argon gas, for example, is used as a plasma stabilizing gas, the emission spectrum of carbon monoxide or a $CO^+$ ion nearly overlaps the emission spectrum of argon gas in a wavelength band of 350 to 860 nm. However, in a wavelength band of 210 to 236 nm, the emission spectrum of carbon monoxide or a $CO^+$ ion can be singly detected since there is no emission spectrum of argon gas in that wavelength band. Therefore, by selecting a wavelength band in this way and calculating the sum average value of an emission spectrum in the selected wavelength band to detect its variation, it is possible to detect a variation in the quantity of carbon monoxide in the process chamber. In addition, carbon monoxide or a $CO^+$ ion has intrinsic emission spectra at wavelengths of particularly 219.0 nm, 230.0 nm, 211.2 nm, 232.5 nm, and 224 to 229 nm. Therefore, the end point of a plasma process can be determined directly on the basis of the peak values of the emission intensities at these wavelengths.

Taking into account the foregoing, in order to eliminate noise resulting from the emission spectrum of silicon and to detect the emission spectrum of a $CF_2$ radical obtained by dissociation of $CHF_3$, the spectroscope 91 is so designed as to perform detections in, e.g., a wavelength band of 240 to 350 nm, preferably 240 to 280 nm, and more preferably 255 to 287 nm. Also, the spectroscope 92 is so designed as to detect the peak value of an emission intensity in, e.g., a wavelength band of 210 to 236 nm or at a wavelength of 219.0 nm.

The light components transmitted from these spectroscopes 91 and 92 are converted into electrical signals corresponding to their respective wavelength spectra by the controller 76. In this case, the sum average value of an emission spectrum in a certain wavelength band is calculated, and the peak value of an emission spectrum having the peak value of an emission intensity at a certain wavelength is directly used. The determination unit 97 performs predetermined calculations by using these values and determines the end point of the etching on the basis of the calculated values.

The determination of the end point of etching is briefly described below. That is, this arithmetic unit performs calculations in such a manner that the slopes of variation curves indicating the sum average values of the emission intensities of the emission spectra of objective species in a certain wavelength band or the peak values of the emission intensities of these emission spectra at a certain wavelength agree with each other, thereby obtaining a coefficient. Subsequently, the arithmetic unit uses this coefficient to perform predetermined calculations for an emission intensity obtained after that and calculates the ratio of the emission intensities. The end point of etching is determined when the value of the ratio exceeds a predetermined reference value.

Figure 19A:
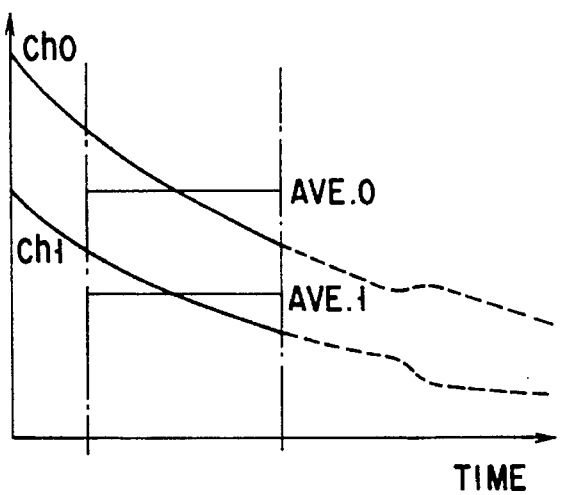
FIGS. 19A to 19C are graphs for explaining examples of calculations to be performed in a dry etching process using an end point detection method according to the present invention.
Figure 19B:
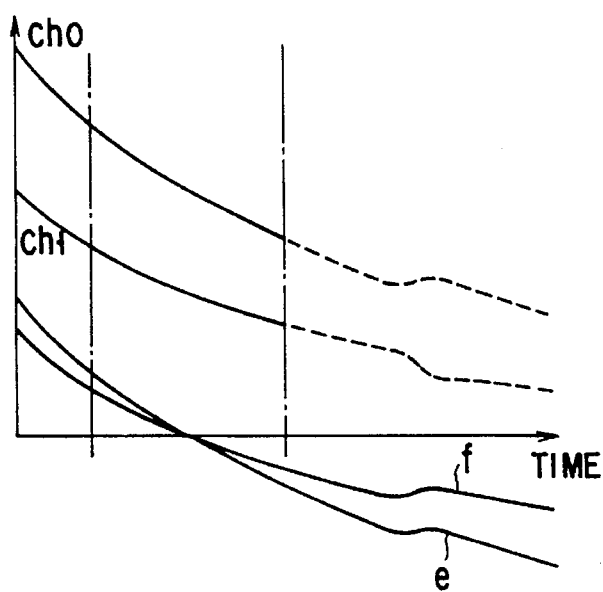
Figure 19C:
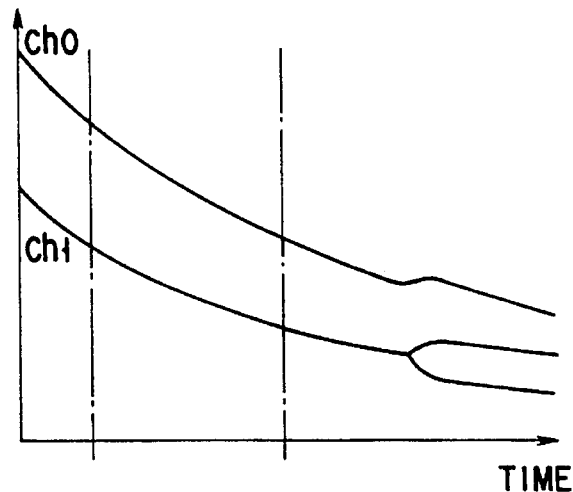

More specifically, the emission intensities (or the sum average values of the emission intensities) of light obtained by the spectroscopes 91 and 92 so change as to plot the variation curves as in FIGS. 19A to 19C as etching proceeds. Note that FIG. 19A shows a change (corresponding to an output $Ch_0$ from the photoelectric converter 93) in an emission intensity (or its sum average value) related to an active species, and a change (corresponding to an output $Ch_1$ from the photoelectric converter 94) in an emission intensity (or its sum average value) related to a produced gas.

The determination unit 97 performs the following calculations.

(1) Average values $AVE_0$ and $AVE_1$ in a designated interval of such variation curves are calculated.

(2) The absolute values of differences between N measured values $Ch_0$ and $Ch_1$ and the average values $AVE_0$ and $AVE_1$, respectively, in the designated interval are calculated to obtain designated interval averages $A_0$ and $A_1$ (an area calculation).

(3) A ratio R of the designated interval averages $A_0$ to $A_1$ is calculated. The designated interval averages $A_0$ and $A_1$ and the ratio R are calculated for the above designated interval.

(4) The average value $AVE_0$ is subtracted from the output $Ch_0$ of the photoelectric converter 93 to obtain $Ch'_0$ (a curve e in FIG. 19B).

(5) $Ch'_0$ is divided by the ratio R to obtain $Ch''_0$ (a curve f in FIG. 19B). Consequently, the slope of the curve indicating $Ch_0$ and the slope of the curve indicating $Ch_1$ agree with each other.

(6) $Ch'''_0$ is calculated by adding an average value $Ave1$ of $Ch_1$ to $Ch''_0$. Consequently, this agrees with the curve indicating $Ch_1$.

(7) A ratio r of the calculated value $Ch'''_0$ to the output $Ch_1$ is calculated. If the value of the ratio r changes to exceed a predetermined reference value (threshold value) which has been set beforehand, this point is determined as the end point of the etching.

In the above calculations, the output $Ch_0$ is converted using the coefficient. Instead, it is also possible to convert the output $Ch_1$ by the coefficient. The calculations performed by the determination unit 97 are not limited to those of the above method. As an example, it is possible to obtain approximate curves of the variation curves of the two outputs and calculate the ratio by making the slopes of these approximate curves agree with each other.

On the basis of this determination of the determination unit 97, the etching process is terminated automatically or by a command from an operator. If an object to be processed requires overetching, a program for that purpose is stored beforehand in the determination unit 97. In this case, etching can be terminated when a predetermined overetching time elapses after the end point of the etching is determined.

Figure 20:
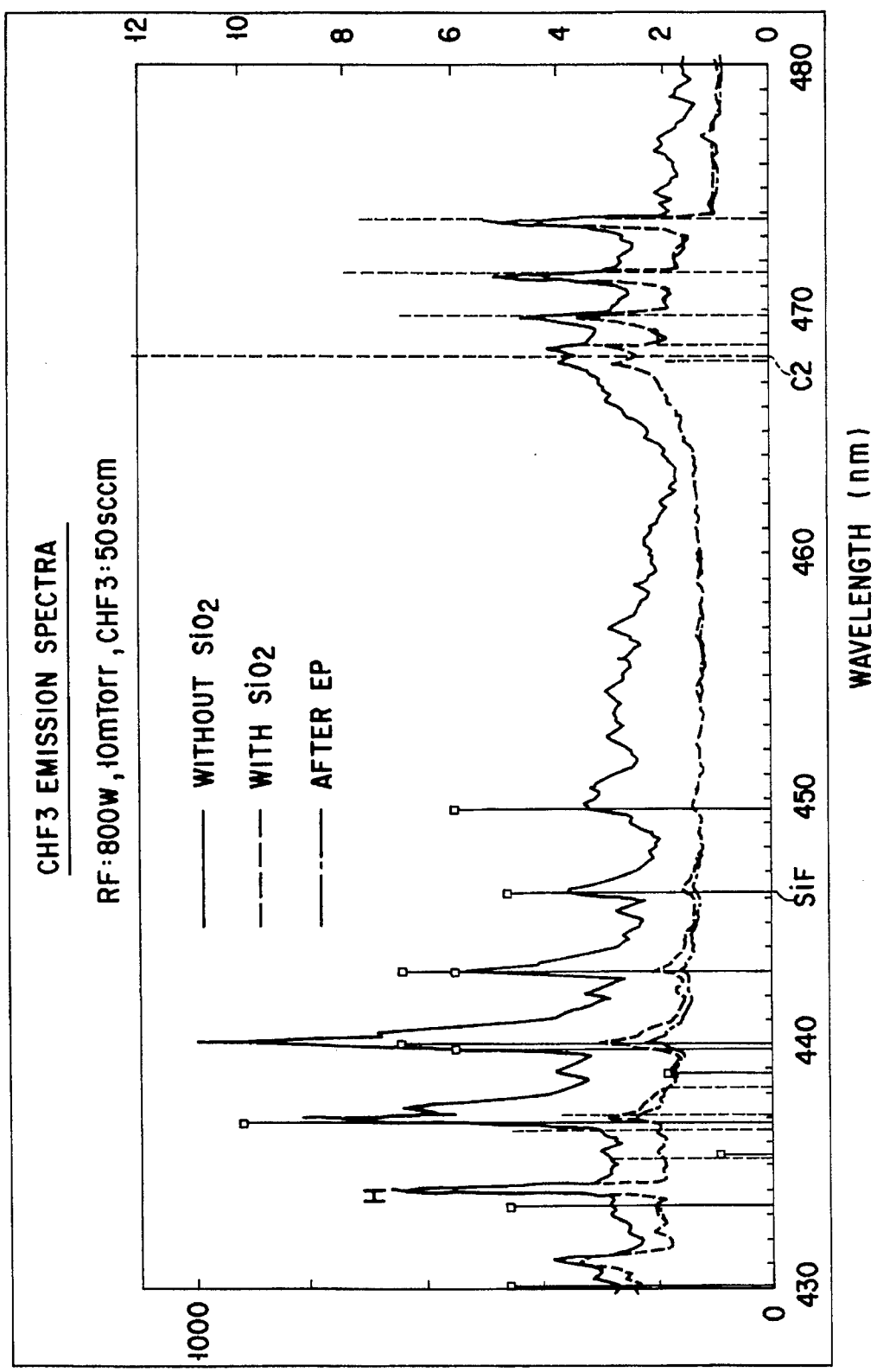
FIG. 20 is a graph showing the emission intensity distributions of emission spectra in a wavelength band of 430 to 480 nm when etching was performed on a silicon oxide film by using $CHF_3$ gas at a process pressure of 10 mTorr.

This embodiment has been described by taking detection of the emission spectrum of carbon monoxide as a reaction product as an example. However, the embodiment is not limited to this example. In performing a low-pressure process, for instance, the emission spectrum of an SiF radical as in FIG. 20 can be used in the end point detection for a plasma etching process. In that case, a wavelength band to be monitored can be set to 430 to 450 nm. Alternatively, it is possible to use the peak value of the emission intensity of an SiF radical at a specific wavelength of 436.8 nm, 438.8 nm, 440.05 nm, or 443.0 nm in the determination.

In addition, this embodiment has been described by taking etching performed for a silicon oxide film as an example. However, the embodiment is not limited to such etching but can be applied to etching for, e.g., a polysilicon film or an aluminum alloy film. Also, the underlying film of a film to be etched may consist of a substance other than single-crystal silicon. An example is polysilicon.

Furthermore, this embodiment is applicable to an etching system of either a cathode coupling type in which an object to be processed is placed on the cathode side or an anode coupling type in which it is placed on the anode side. This embodiment is also applicable to an etching process by which a reactive gas plasma is generated in a discharge region by using an additionally provided thermionic source and this reactive gas plasma is introduced to an etching region. This embodiment is also applicable to an inductive coupled type etching apparatus.

As has been discussed above, in the end point detection method based on this embodiment, the emission spectrum of an active species to be monitored is monitored not by the peak value of the emission intensity of that active species but over an emission spectral range which has a certain fixed width and within which the peak value of the emission intensity of that active species does not overlap the peak values of the emission intensities of other active species, i.e., over an emission spectral range within which the influence of the emission of other active species is negligible. Therefore, detection can be performed with a large quantity of light as a whole even if the quantity of light at each individual wavelength is small. This makes it possible to perform plasma process end point detection with a high S/N ratio and a high accuracy even if a photodetector with a low sensitivity is used.

EXAMPLE 4

It is difficult for a plasma process system having parallel plate electrodes to perform ultra-fine processing of submicron and subhalfmicron orders, which has been required as the degree of integration of semiconductor devices has increased tremendously. To perform such ultra-fine processing by plasma process systems of this type, it is important to control a high-density plasma at a high accuracy in a low-pressure atmosphere. Additionally, this plasma must be uniform in a large area in order to process large-diameter semiconductor wafers. Also, in a plasma process system of the above sort, the electrodes themselves act as heavy metal contamination sources upon generation of a plasma. This is a serious problem especially when ultra-fine processing is required.

To meet these technical requirements, various approaches have been made to establish a new plasma source. At present, however, no technique which is simple in structure and meets these high-level technical requirements has been established.

In this embodiment, there is provided a plasma process system which is simple in structure, which forms a high-density plasma which is uniform in a large area in a low-pressure atmosphere, which can control the plasma with a high accuracy, which can avoid heavy metal contamination derived from the electrode material, and which can achieve the end point detection methods described in Examples 1 to 3. More specifically, the plasma process system of this embodiment comprises an antenna means which spirally surrounds a portion of the outer wall of a process chamber above the surface to be processed of an object to be processed, one end of which forms as an open end, and the other end of which is connected to an RF power supply, and grounding means provided in the vicinity of the surface to be processed of the object and consisting of a conductive material, wherein at least the portion of the process chamber surrounded by the antenna means is made from an insulating material which transmits electromagnetic waves.

In the above arrangement, a process gas is activated by applying the energy of an electromagnetic wave from an RF power supply via the antenna means, thereby producing a high-density plasma. This makes it possible to perform a plasma process, such as etching, on the surface to be processed of an object to be processed which is placed near the grounding means. This embodiment makes it unnecessary the use of a waveguide for propagating microwaves or a large-sized component such as an electromagnet for forming a large magnetic field such as one used in conventional ECR systems.

FIG. 21 shows an example of a plasma etching system for performing the end point detection method according to the present invention. This plasma etching system 101 includes a substantially cylindrical process chamber 102 and a loop antenna 103 which spirally surrounds the outer wall of the process chamber 102. The process chamber 102 consists of an insulating material, such as quartz, glass, or silicon carbide, which transmits electromagnetic waves. The loop antenna 103 is made of, e.g., copper. A lower end 103A of the loop antenna 103 forms as an open end, and its upper end 103B is connected to an RF power supply 105 via a matching circuit 104. The process chamber 102 is placed on a stainless steel base 106.

A gas inlet pipe 107 for supplying a predetermined process gas, e.g., $CHF_3$ gas from a gas source (not shown) is connected to the center of the top wall of the process chamber 102. An exhaust pipe 108 for evacuating the process chamber 102 by using an exhaust means, e.g., a vacuum pump (not shown) is connected to the lower portion of the process chamber 102 via the base 106. A susceptor 109 for placing an object to be processed, e.g., a semiconductor wafer W is arranged in the center of the process chamber 102. This susceptor 109 is so designed as to be vertically movable between the base 106 and the process chamber 102 by an elevating unit (not shown). A gate valve 110 for allowing a load-lock chamber (not shown) to communicate with the process chamber 102 is provided in the side wall of the base 106. The susceptor 109 is made from a conductive material, such as stainless steel, and is grounded by some appropriate wiring means.

In the plasma etching system with the above construction, the gate valve 110 is opened first, and the object to be processed, e.g., the semiconductor wafer W is transferred by a transfer arm (not shown) from the neighboring load-lock chamber into the process chamber 102 which is already evacuated to a reduced-pressure atmosphere, e.g., a few ten mTorr. The semiconductor waver W is then fixed on the susceptor 109 by a proper fixing means such as an electrostatic chuck. Subsequently, the susceptor 109 is raised to a desired process region and set at that region. Thereafter, a predetermined process gas, e.g., $CHF_3$ gas is supplied from the gas inlet pipe 107 into the process chamber 102, and an RF voltage of, e.g., 13.56 MHz is applied from the RF power supply 105 to the loop antenna 103. The loop antenna 103 radiates the energy of an electromagnetic wave into the process chamber 102. Consequently, the process gas is dissociated into a plasma by this electromagnetic-wave energy. The resultant plasma is irradiated as a plasma stream onto the surface to be processed of the object placed on the grounded susceptor 109. Thus, a plasma process, e.g., an etching process is performed on a silicon oxide film formed on the surface to be processed. When the plasma process is completed, ended, the residual gas in the process chamber 102 is exhausted through the exhaust pipe 108. Thereafter, the susceptor 109 is moved downward, the gate valve 110 is opened, and the processed object is transferred out from the process chamber 102 by the transfer arm (not shown).

As described above, this embodiment can readily generate a high-density plasma which is uniform in a large area in the process chamber 102 in a low-pressure atmosphere without using a waveguide for guiding microwaves or a large-sized component such as an electromagnet for forming a large magnetic field such as used in ECR systems. In addition, since a plasma can be generated without using any electrodes, it is possible to circumvent heavy metal contamination caused by the electrode material.

FIG. 22 shows another example of a plasma etching system for performing the end point detection method according to the present invention. The basic arrangement of this plasma etching system 121 in FIG. 22 is nearly identical with that shown in FIG. 21. Therefore, the same reference numerals as in FIG. 21 denote parts having the same functions in FIG. 22, and a detailed description thereof will be omitted.

As in FIG. 22, a process chamber 122 of the plasma etching system 121 has a top wall which is curved toward the center, and has a substantially cylindrical side wall 122A consisting of an insulating material, such as quartz, which transmits electromagnetic waves. A gas inlet pipe 107 is connected to the center of a curved portion 122B of the process chamber 122. A loop antenna 103 spirally surrounds the cylindrical side wall 122A. A susceptor 109 is grounded and extends through a base 106 made from a conductive material such as stainless steel. The susceptor 109 is connected to an RF power supply 124 via a matching circuit 123 and applied with a bias potential in performing a process.

In this construction, the RF power supply 105 applies an RF power to the loop antenna 103. Consequently, a high-density plasma which is formed in the process chamber 102 and is uniform in a large area can be controlled at a high accuracy by the bias potential applied to the susceptor 109. This permits an etching process with an ultra-high accuracy.

FIG. 23 is a schematic view illustrating a plasma ashing system 131 based on this embodiment. This ashing system 131 includes a dome-like process chamber 132 made from an insulating material, such as quartz or silicon carbide, which transmits electromagnetic waves. A gas inlet pipe 140 is connected to the top wall of the dome of the process chamber 132. The gas inlet pipe 140 can supply a predetermined process gas, e.g., a gas mixture of oxygen and a freon-based gas, from a gas source (not shown). A loop antenna 133 consisting of, e.g., copper is spirally wound on the outer wall of the process chamber 132. A lower end 133A of the antenna 133 forms an open end, and its upper end 133B is connected to an RF power supply 135 via a matching circuit 134. In addition, a susceptor 136 capable of placing an object to be processed, e.g., a semiconductor wafer W on it is arranged in the center of the process chamber 132. This susceptor 136 is made from a conductive material, such as stainless steel, and is grounded by some appropriate wiring means. The susceptor 136 can be moved vertically by an elevating unit (not shown), and so the object to be processed can be set at a desired position.

The process chamber 132 with the above arrangement is placed on a base 137 consisting of, e.g., stainless steel. A gate valve 138 for allowing a load-lock chamber (not shown) to communicate with the process chamber 132 is provided in the side wall of the base 137. Also, the process chamber 132 can be evacuated to a predetermined reduced-pressure atmosphere through an exhaust pipe 139 connected to the base 137.

In the plasma ashing system having the above arrangement, the process chamber 132 is first evacuated to a predetermined reduced-pressure atmosphere, e.g., a few ten mTorr by an exhaust means (not shown) through the exhaust pipe 139. The object to be processed is then transferred into the process chamber 132 from the adjacent load-lock chamber through the bate valve 138. The transferred object is fixed on the susceptor 136 in the base 137 and moved up to a predetermined process region in the process chamber 132 by raising the susceptor 136. Subsequently, a predetermined process gas, e.g., a gas mixture of oxygen and a freon-based gas is supplied from the gas inlet pipe 140 into the process chamber 132, and an RF power of, e.g., 13.56 MHz is applied from the RF power supply 135 to the loop antenna 133. Consequently, the energy of an electromagnetic wave is supplied into the process chamber 132, and the process gas is activated by this electromagnetic-wave energy, thus generating a plasma. With this plasma, a photoresist formed on the surface to be processed of the object is ashed. When the plasma process is ended, the residual gas is exhausted, and the susceptor 136 is moved down to the base 137. Thereafter, the gate valve 138 is opened, and the processed object is transferred by a transfer arm (not shown).

In this embodiment as discussed above, no plasma generator need be provided in addition to the plasma process unit. That is, the loop antenna is spirally wound on the outer wall of the process chamber made of an insulating material which transmits electromagnetic waves, and an RF power is applied to this loop antenna. Consequently, it is readily possible to generate a high-density plasma which is uniform in a large area in the process chamber. This makes it possible to simplify and miniaturize the construction of the system.

In this embodiment, it is also possible to use loop antennas with structures as illustrated in FIGS. 24 and 25. Note that the portion for applying an RF voltage to the loop antenna is omitted from FIGS. 24 and 25.

When any of the plasma process systems illustrated in FIGS. 21 to 23 is operated, an RF power of, e.g., 13.56 MHz is applied. Therefore, heat of the copper loop antenna may damage the antenna itself or the process chamber. To avoid this event, it is preferable to use a structure which cools the loop antenna. More specifically, as in FIG. 24, a heat-resistant insulating pipe 141 is inserted into a hollow loop antenna 140. Cooling water is flowed through this pipe 141 from an RF power application side 142 to an open end side 143, thereby preventing overheating of the loop antenna. Alternatively, as in FIG. 25, two holes 151 and 152 which communicate with each other on an open end side 153 of a loop antenna 150 to form a closed circuit are formed in the antenna 150, and a heat-resistant insulating pipe 154 is inserted through these holes. Cooling water is circulated through the antenna 150 by supplying it from one hole 151 on an RF voltage application side 155 of the antenna 150 and recovering it from the other hole 152. In this manner, it is possible to prevent overheating of the loop antenna 140 or 150 and to ensure a stable operation of the system.

Although a plasma etching system and a plasma ashing system have been described in this embodiment, the embodiment is not restricted to these systems. For example, the embodiment is also applicable to a sputtering system, an ion injection system, and a plasma CVD system. It is also possible to make various modifications that can be made by those skilled in the art.

In this embodiment, the use of the end point detection methods of Examples 1 to 3 allows not only generation of a high-density plasma which is uniform in a large area but also an accurate determination of the end point of a plasma process.

EXAMPLE 5

In performing end point detection in a plasma process system, the emission spectrum of a plasma is monitored through a window which is a transparent member formed in a process chamber. When the plasma process is executed a number of times, the reaction products of the plasma process adhere to the window, and this decreases the input light to a photodetector. The result is a low accuracy of the end point detection. For this reason, the window must be cleaned at proper intervals. In a plasma process system, on the other hand, it is necessary to perform processes in a predetermined reduced-pressure atmosphere. This requires the process chamber to be highly airtight. Therefore, the window is mounted in the side wall or the like of the process chamber via a sealing member such as an O-ring.

There is one conventional technique which suppresses adhesion of reaction products to the window by providing a heating means to the window. In this technique, however, the sealing member may be thermally deformed by the heating means. If the sealing member thermally deforms, the airtightness of the process chamber is degraded, making a predetermined plasma process impossible to result in a low yield. Also, the heating efficiency is low if the heating means such as a heater merely provided to the window.

This embodiment, therefore, provides an end point detection method which can accurately detect the end point of a plasma process by removing reaction products efficiently without adversely affecting a sealing member. More specifically, there is provided an end point detection method performed by using a plasma process system comprising a transparent member which is provided in the side wall of a process chamber via a sealing member and transmits plasma emission generated in the process chamber to outside the process chamber, a heating unit which is provided in the transparent member and heats the transparent member, and a light-receiving unit for receiving the plasma emission transmitted through the transparent member, wherein a groove is formed in a portion of the transparent member between the sealing member and the heating unit from inside the process chamber. In this method, transfer of heat from the heating unit is interrupted by the groove, and this prevents easy conduction of the heat to the material, e.g., quartz glass which forms the transparent member. Consequently, the quantity of heat conducted from the heating unit to the sealing member is largely reduced. In addition, since the conduction of heat is prevented by the groove, the quantity of heat to be radiated to the surrounding components is decreased. This makes it possible to efficiently heat the transparent member.

In this embodiment, it is preferable that the heating unit be provided in the groove which is formed from outside the transparent member, and that a filler with a high thermal conductivity be provided between the heating unit and the inner walls of the groove. With this arrangement, the transparent member is heated at a higher efficiency.

Figure 26:
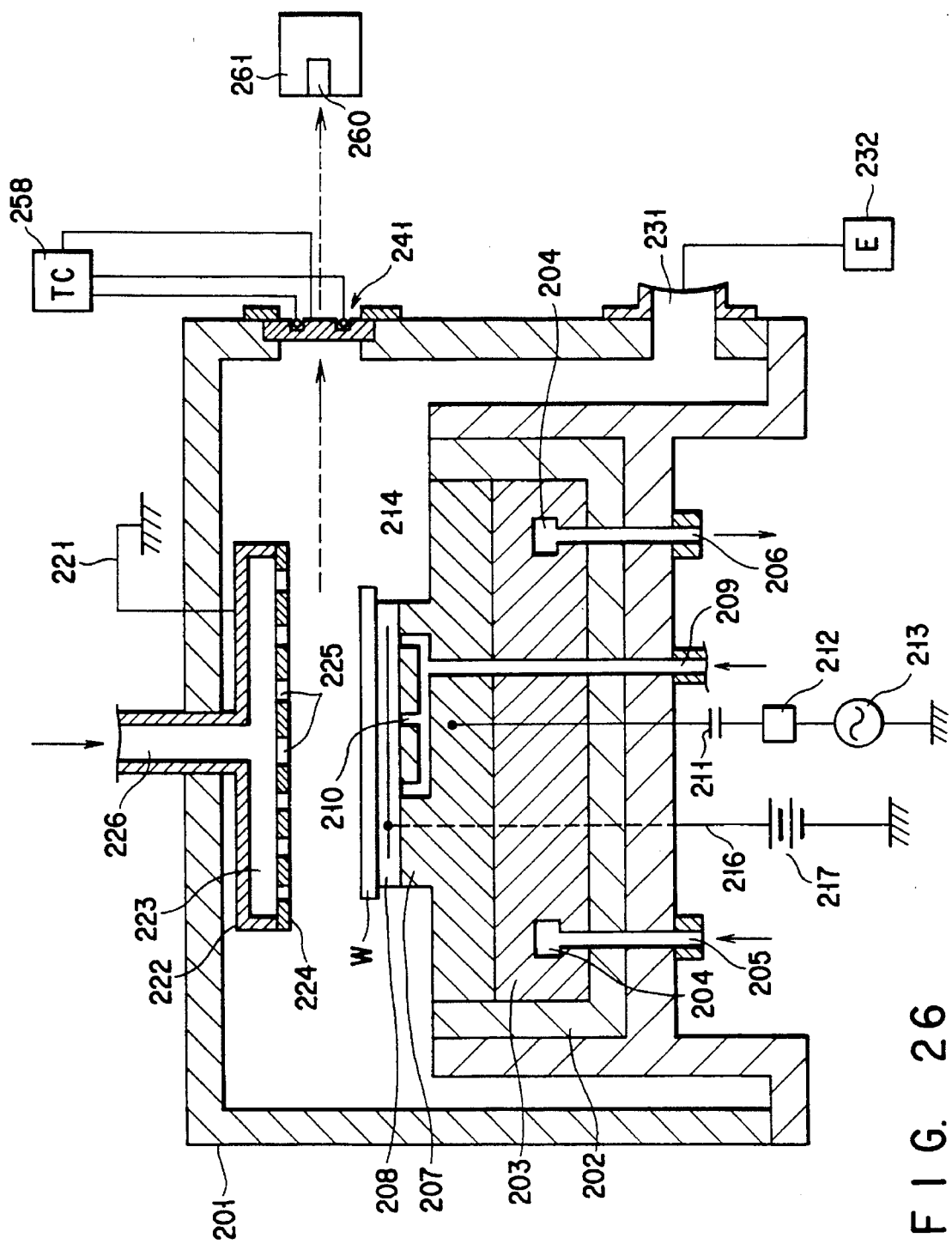

FIG. 26 is a view for explaining an example of a plasma etching system for use in the end point detection method of this embodiment. An airtightly closable process chamber 201 is a substantially cylindrical member consisting of, e.g., aluminum whose surface is subjected to anodization. In the lower portion of the process chamber 201, a susceptor support table 203 is provided via an insulating member 202 consisting of, e.g., ceramics. A cooling chamber 204 such as a cooling jacket is formed inside the susceptor support table 203. A coolant circulating mechanism is also provided in the cooling chamber 204. In this coolant circulating mechanism, a coolant is fed from a coolant inlet pipe 205 formed in the bottom of the process chamber 201 and discharged from a coolant outlet pipe 206.

A susceptor 207 consisting of, e.g., aluminum whose surface is subjected to anodization is provided on the upper surface of the susceptor support table 203. The susceptor 207 constitutes a lower electrode. An electrostatic chuck 208 on which a wafer W as an object to be processed is placed is provided on the upper surface of the susceptor 207.

Inside the susceptor 207, a gas flow path 210 which communicates with a gas inlet pipe 209 is formed. By supplying, e.g., He gas from a separately provided gas supply unit (not shown) to the gas inlet pipe 209, this He gas can be supplied to the gas flow path 210. In this case, coldness from the susceptor support table 203 which is set at a predetermined temperature by the coolant is conducted to the He gas. By the He gas cooled this way, the semiconductor wafer W placed on and held by the electrostatic chuck 208 is cooled to a predetermined temperature. The susceptor 207 is connected to an RF power supply 213, outside the process chamber 201, via a blocking capacitor 211 and a matching circuit 212. This RF power supply 213 applies an RF power of, e.g., 13.56 MHz to the susceptor.

The electrostatic chuck 208 has a structure in which insulating bodies such as polyimide films are adhered to the upper and lower surfaces of a conductive layer 214 consisting of, e.g., an electrolytic copper foil. This conductive layer 214 is connected to a high-voltage DC power supply 217 outside the process chamber 201 through a supply lead wire 216. When the high-voltage DC power supply 217 applies a DC voltage to the conductive layer 214, the wafer W is attracted to and held by the electrostatic chuck 208 by a consequent Coulomb force.

In the upper portion of the process chamber 201, an upper electrode 222 which is grounded through a ground wire 221 is provided. This upper electrode 222 has a hollow portion 223 and an opposing surface 224 which opposes the susceptor 207. The opposing surface 224 is made of a material such as amorphous carbon. A large number of discharge holes 225 communicating with the hollow portion 223 are formed in the opposing surface 224. A gas inlet port 226 communicating with the hollow portion 223 is also provided in the upper portion of the upper electrode 222. Therefore, when a process gas is supplied from a separately provided process gas supply unit (not shown) to the gas inlet port 226, this process gas is discharged uniformly from the discharge holes 225 toward the susceptor 207.

An exhaust system of the process chamber 201 is as follows. An exhaust pipe 231 is provided in the vicinity of the bottom of the process chamber 201 and connected to an exhaust means 232 such as a vacuum pump. By the operation of this exhaust means 232, the process chamber 201 can be evacuated and maintained in a predetermined reduced-pressure atmosphere, e.g., at 0.5 Torr.

Figure 27:
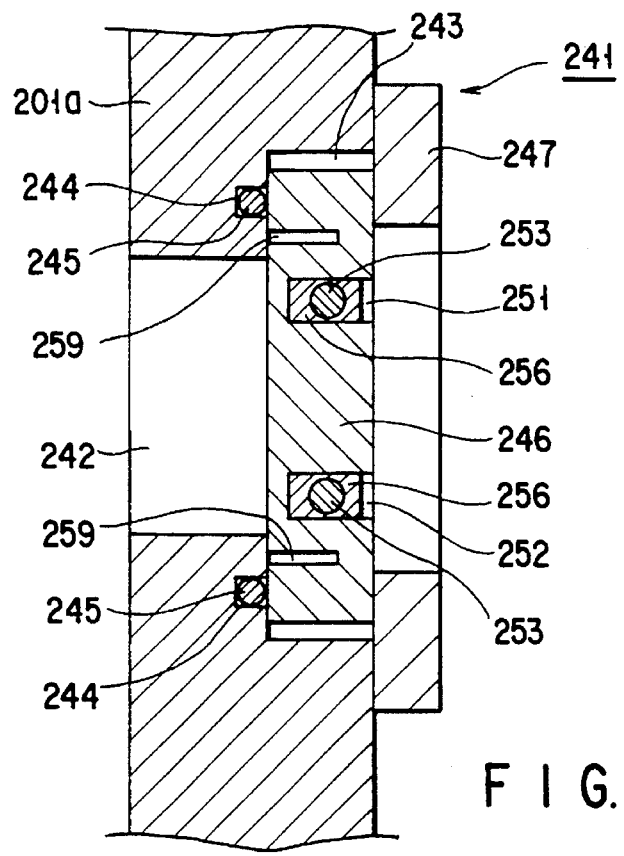
FIG. 27 is an enlarged view of major components of the plasma process system in FIG. 26.

A window unit 241 as shown in FIG. 27 is formed in a side wall 201a of the process chamber 201. This window unit 241 has the following structure. That is, a hole 242 is formed to extend through the side wall 201a. In addition, a recess portion 243 larger than the hole 242 is formed outside the hole 242. A fitting groove 244 is formed in the side wall of the process chamber 201 in this recess portion 243 so as to surround the hole 242. An O-ring 245 is fitted in this fitting groove 244, and a transparent member 246 is fitted in the recess portion 243 from outside the O-ring 245. Also, an appropriate mounting member 247 is fixed to be pushed against the side wall 201a from outside the transparent member 246, thereby fixing the transparent member 246 to the side wall 201a.

The transparent member 246 consists of a material such as quartz glass and has the shape of a rectangular parallelpiped as a whole. The transparent member 246 is slightly smaller than the recess portion 243. Therefore, even if the transparent member 246 expands upon heating, this expansion is tolerable, and as a consequence damages are prevented. Two, upper and lower mounting grooves 251 and 252 are formed in the outer surface of the transparent member 246. A bar cartridge heater 253 as a heating unit is mounted in each of the mounting grooves 251 and 252.

Figure 28:
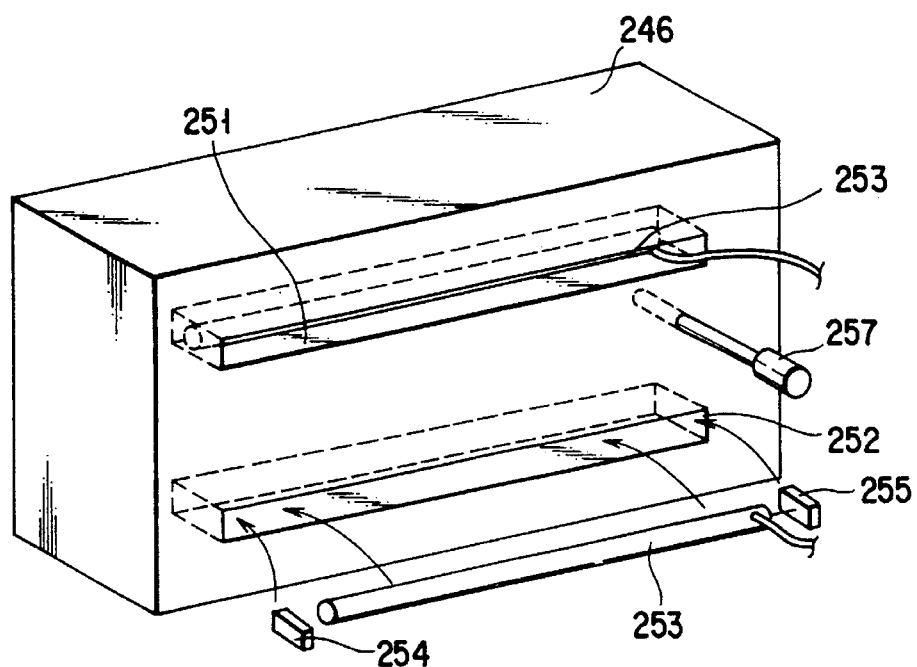
FIG. 28 is a perspective view of a transparent member of the plasma process system in FIG. 26.

This mounting is done as follows. That is, as in FIG. 28, the cartridge heater 253 is placed in the mounting groove 251 (252) with silicone rubber members 254 and 255 attached to both the ends of the cartridge heater 253. Subsequently, as in FIG. 27, heat-transfer cement 256 is filled between the cartridge heater 253 and the inner walls of the mounting groove 251 (252), thereby filling the gaps between them and fixing the heater. This heat-transfer cement 256 has a heat resistance of about 400° C. and consists of a material having a very high thermal conductivity.

The transparent member 246 further includes a temperature detector 257 constituted by a thermocouple or the like. A detection signal from the temperature detector 257 is supplied to a temperature controller 258 shown in FIG. 26. The temperature controller 258 controls the cartridge heaters 253 on the basis of this detection signal. Consequently, the transparent member 246 is set to and maintained at an arbitrary temperature between, e.g., +100° C. and +300° C.

As illustrated in FIGS. 27, 29, and 30, a heat-insulating groove 259 for interrupting heat transfer is formed in the surface of the transparent member 246 on the process chamber 201 side. As in FIG. 30, this heat-insulating groove 259 is formed between a portion A (a hatched portion in FIG. 30) in contact with the O-ring 245 and the two cartridge heaters 253 so as to surround the cartridge heaters 253. Outside the window unit 241 with this arrangement, an end point detection apparatus 261, in FIG. 26, is arranged. The end point detection apparatus 261 comprises a photodetector 260 for detecting, through the transparent member 246, plasma emission generated between the susceptor 207 and the upper electrode 222 in the process chamber 201.

In the plasma etching system having the above arrangement, a gate valve (not shown) provided in the side wall of the process chamber 201 is first opened, and the wafer W is transferred into the process chamber 201 by a transfer unit (not shown) such as a transfer arm. The wafer W is then placed at a predetermined position on the electrostatic chuck 208, and the transfer unit is moved outside the process chamber 201. Thereafter, the wafer W is attracted to and held by the electrostatic chuck 208 by application of a DC voltage from the high-voltage DC power supply 217.

Subsequently, a process gas, such as $CF_4$ gas, is supplied from the process gas supply unit to the gas inlet port 226 and discharged toward the wafer W from the discharge holes 225 of the upper electrode 222. At the same time, the exhaust means 232 is operated to maintain the internal pressure of the process chamber 201 at, e.g., 0.5 Torr. The RF power supply 213 then applies an RF power at, e.g., a frequency of 13.56 MHz and a power of 1 kW to the susceptor 207. Consequently, a plasma is generated between the upper electrode 222 and the susceptor 207 to perform a predetermined etching process on the wafer W.

The emission of this plasma is detected by the photodetector 260 of the end point detection apparatus 261 through the transparent member 246 of the window unit 241, and thereby the end point of the plasma etching process is determined. Assuming the emission intensity in a plasma steady state is 100, for example, a point at which the emission intensity drops to 60 is determined as the end point of the plasma etching. In this case, the surface of the transparent member 246 on the process chamber 201 side is heated to, e.g., 200° C. by the cartridge heaters 253 in order to prevent adhesion of the reaction products. The conduction of this heat is interrupted by the heat-insulating groove 259 formed between each cartridge heater 253 and the O-ring 245. Consequently, the heat does not conduct easily to the O-ring which ensures the airtightness between the transparent member 246 and the side wall 201a of the process chamber 201. Therefore, the quantity of heat conducted to the O-ring 245 is largely decreased to prevent a large increase in the temperature of the O-ring 245, with the result that no thermal deformation takes place. As a consequence, the airtightness between the transparent member 246 and the side wall 201a of the process chamber 201 is well maintained.

Additionally, the radiation of heat is suppressed because the conduction of heat is interrupted by the heat-insulating groove 259. Therefore, a region to be heated by the cartridge heaters 253 is primarily the region surrounded by the heat-insulating groove 259, so this region can be heated efficiently. Furthermore, the heat-transfer cement 256 with a high thermal conductivity is filled between each cartridge heater 253 and the inner walls of the mounting groove 251 (252) of the transparent member 246. Consequently, heat generated directly by the cartridge heaters 253 is conducted efficiently to the transparent member 246. This further improves the heating efficiency of the cartridge heaters 253 with respect to the region to be heated. Also, the silicone rubber members 254 and 255 are attached to both the ends of each cartridge heater 253. The combination of the silicone rubber members 254 and 255 and the heat-transfer cement 256 makes it possible to stably mount each cartridge heater 253 in the mounting groove 251 (252) without any looseness. In addition, the silicone rubber members 254 and 255 allow the expansion of the cartridge heater 253 itself upon heating. Therefore, the transparent member 246 can be protected against damages even if an excess pressure is applied on the inner walls of the mounting grooves 251 and 252 due to the expansion of the cartridge heaters 253.

In this embodiment as described above, the transparent member 246 has a simple arrangement, and this prevents the influence of heat upon the O-ring 245 which assures the airtightness between the transparent member 246 and the side wall 201a of the process chamber 201. This also makes it possible to largely improve the heating efficiency of the cartridge heaters 253. As a consequence, it is possible to efficiently heat the transparent member and to thereby suppress adhesion of reaction products to the window.

Although this embodiment has been discussed by taking a plasma etching system as an example, the embodiment is not limited to this system. For example, the embodiment is also applicable to other plasma process systems, such as an ashing system and a CVD system.

EXAMPLE 6

A window as a transparent member is fixed to the side wall of a process chamber in the following manner. That is, a plate-like transparent member with a size larger than that of a through hole formed in the side wall of a process chamber is pushed against the peripheral portion of the through hole from outside (from the atmosphere) by a proper mounting member. Therefore, the transparent member protrudes into the side wall of the process chamber; in other words, a recess portion is formed in the inner wall of the process chamber. When a recess portion is formed in the inner wall of the process chamber as in this case, the state of a plasma generated inside the process chamber tends to be nonuniform. This may give rise to abnormal discharge at the corners of the recess portion, and may make a predetermined plasma process impossible.

On the other hand, to observe the state of a plasma or detect the emission of a plasma, the transparent member must be so provided that an object to be processed placed on a table in the process chamber can be seen. In addition, in order to increase the accuracy of the end point detection for a plasma process, the transparent member must be so mounted, by taking account of the refraction of transmitted light or the like, that the optical axis of plasma emission transmitted through the transparent member is perpendicular to the surface of the transparent member. However, so long as a plate-like transparent member is used, the position of the through hole and the transparent member is necessarily restricted to almost the center of the side wall of the process chamber. This consequently limits the layout of a photodetector of an end point detection apparatus or other components or members such as a valve.

This embodiment, therefore, provides a method by which a plasma process can be stably performed without adversely affecting the state of a plasma in a process chamber, and the end point of the plasma process can be accurately detected. More specifically, this embodiment provides an end point detection method characterized by using an end point detection apparatus comprising a transparent member which is provided in a through hole formed in the side wall of a process chamber from outside the process chamber and transmits plasma emission generated in the process chamber to outside the process chamber, and a light-receiving unit for receiving the plasma emission transmitted through the transparent member, wherein the transparent member has a shape that can be fitted in the through hole, and the major surface of the transparent member on the process chamber side is leveled with the inner surface of the side wall.

In this embodiment, the major surface, on the process chamber side, of the transparent member for transmitting the plasma emission in the process chamber to the outside is so molded as to be flush with the inner surface of the side wall of the process chamber. Therefore, no recess portion is formed in the inner wall of the process chamber. This makes it possible to perform the end point detection of a plasma process without influencing the state of a plasma generated in the process chamber. Additionally, since the major surface of the transparent member on the process chamber side is leveled with the inner surface of the side wall of the process chamber, it is possible to provide the transparent member such that the optical axis of plasma emission is perpendicular to the transparent member at any position throughout the entire circumference of the inner wall of the process chamber, even if the inner wall of the process chamber is curved. Therefore, the transparent member can be provided at any arbitrary position of the side wall of the process chamber. This accordingly increases the degree of freedom in the position of a photodetector for detecting the plasma emission from the transparent member or in the layout of a plasma state monitoring unit or other components necessary for the plasma process system.

FIG. 31 is a view for explaining a plasma etching system for use in the end point detection method of this embodiment. The same reference numerals as in FIG. 26 denote the same parts in FIG. 31, and a detailed description thereof will be omitted.

Figure 32:
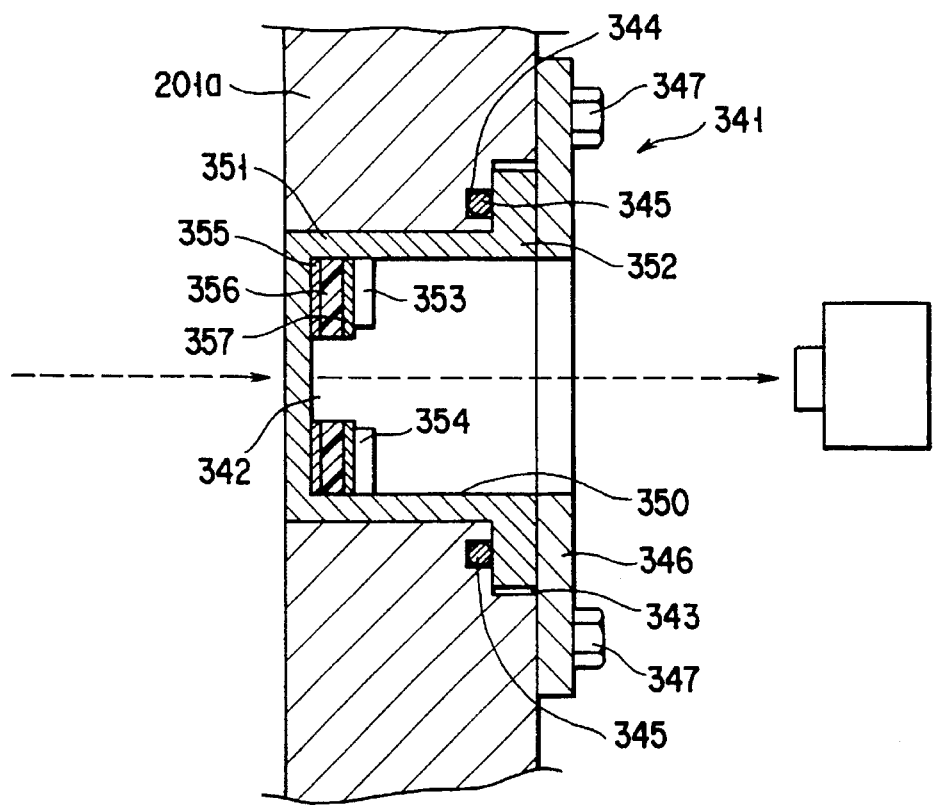
FIG. 32 is an enlarged view of major components of the plasma process system in FIG. 31.

A window unit 341 as shown in FIG. 32 is provided in a side wall 201a of a process chamber 201. This arrangement will be described in detail below. A through hole 342 whose opening has a substantially elongated elliptic shape is formed in the side wall 201a. A recess portion 343 larger than the through hole 342 is formed outside the through hole 342. A fitting groove 344 is formed in a portion of the side wall surface of the process chamber 201 in this recess portion 343 so as to surround the through hole 342. An O-ring 345 is fitted in the fitting groove 344. A fitting portion 351 of a transparent member 350 is fitted in the through hole 342, and a locking portion 352 of the fitting portion 351 is locked in the recess portion 343. An appropriate mounting member 346 is fixed to be pushed against the side wall 201a from outside the locking portion 352 by bolts 347.

Figure 33:
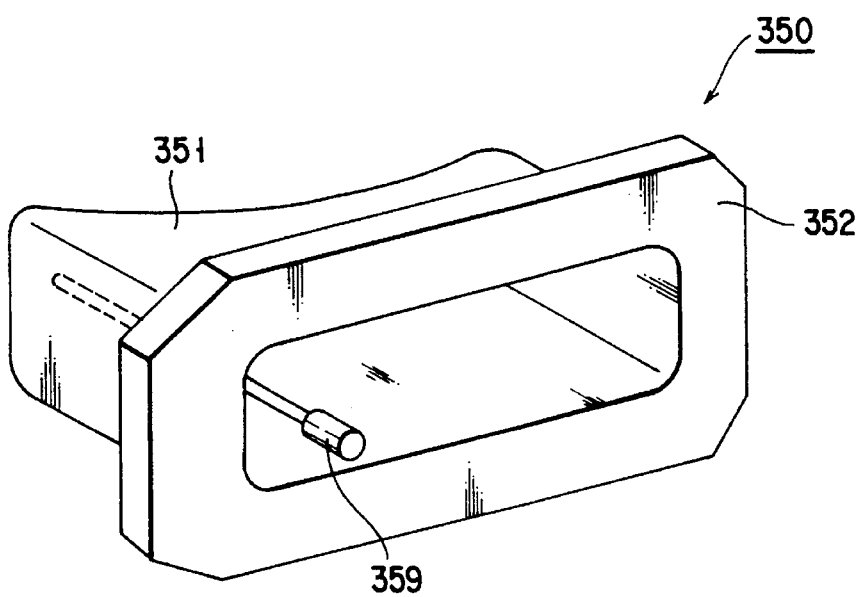
FIG. 33 is a perspective view of a transparent member of the plasma process system in FIG. 31.
Figure 34:
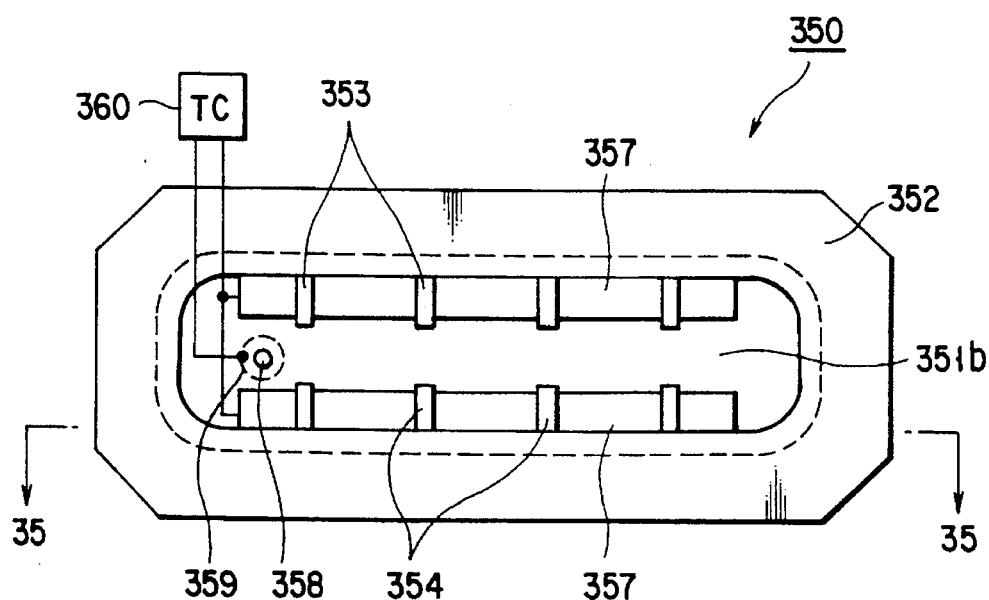
FIG. 34 is a front view of the transparent member of the plasma process system in FIG. 31.
Figure 35:
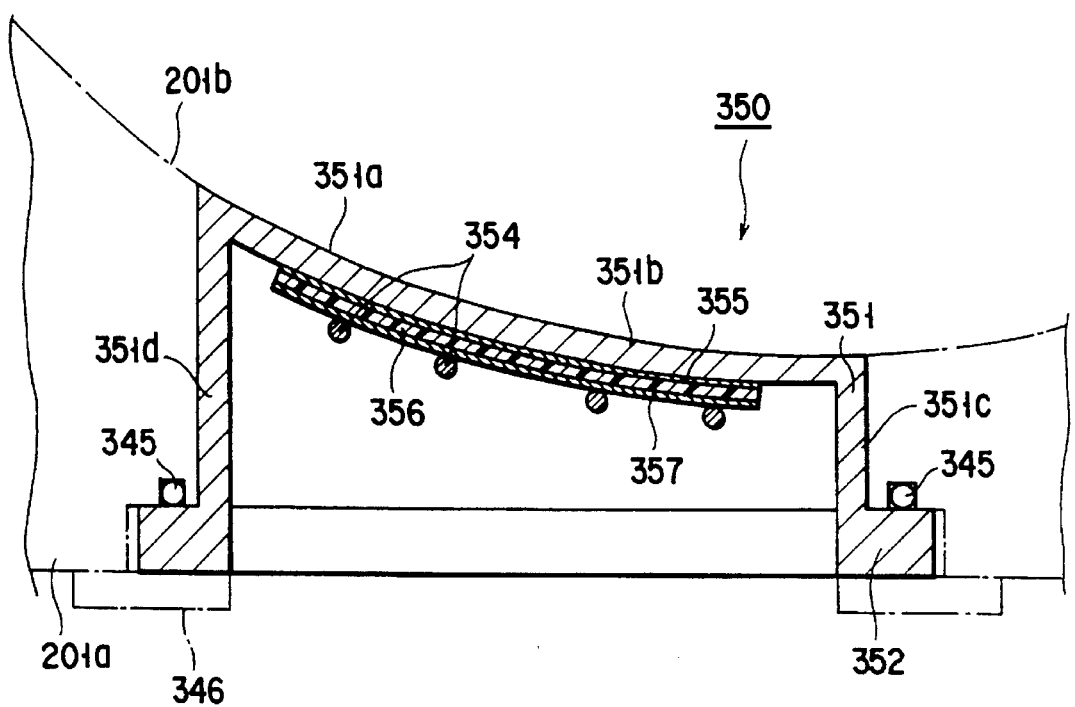
FIG. 35 is a sectional view taken along the line 35—35 in FIG. 34.

The transparent member 350 has a shape shown in FIGS. 33, 34, and 35. The entire outer shape of the transparent member 350 is formed by the locking portion 352 and the fitting portion 351 extending at right angles from the locking portion 352. The material of the transparent member 350 is, e.g., quartz glass. As in FIG. 35, an end face 351a of the fitting portion 351 on the process chamber 201 side is molded into a curved surface with the same curvature as that of an inner circumferential surface 201b of the side wall 201a. When this fitting portion 351 is fitted in the through hole 342, therefore, the end face 351a and the inner circumferential surface 201b of the side wall 201a are flush with each other.

An arbitrary number of, e.g., four locking pins 353 and the same number of locking pins 354 are so formed as to oppose each other on the upper and lower inner surfaces, respectively, of the fitting portion 351. These locking pins 353 or 354 are arranged with predetermined intervals between them along an end wall 351b of the fitting portion 351. Tape-like heaters 355 are adhered to the inner surface of the end wall 351b at positions between the end wall 351b and the locking pins 353 and between the end wall 351b and the locking pins 354. Silicone rubber 356 and a cover plate 357 consisting of, e.g., a thin stainless steel plate are pressed between each heater 355 and the locking pins 353 or 354. Since each heater 355 is provided in the transparent member 350 in this manner, no positional deviation occurs.

In addition, as in FIG. 34, a non-through hole 358 is formed in the end wall 351b of the fitting portion 351, and a temperature sensor 359 is mounted in this hole 358. A detection signal from this temperature sensor 359 is supplied to a temperature controller 360. The temperature controller 360 controls the heaters 355 on the basis of this detection signal. Consequently, the end wall 351b of the fitting portion 351 of the transparent member 350 is set to and kept at a given temperature between, e.g., +100° C. and +300° C.

As shown in FIGS. 31 and 36, an end point detection apparatus 362 is arranged outside the window unit 341 including the transparent member 350 with the above construction. This end point detection apparatus 362 includes a photodetector 361 for detecting, through the end wall 351b of the fitting portion 351 of the transparent member 350, plasma emission generated in a process space S in the process chamber 201, i.e., in the space between a susceptor 207 and an upper electrode 222. In this embodiment, as in FIG. 36, the end point detection apparatus 362 is so arranged that the light-receiving axis of the photodetector 361 is located in exactly the center of the process space S, i.e., that a line connecting the center of a wafer W and the center of the window unit 341 is in agreement with the light-receiving axis of the photodetector 361.

In the plasma etching system with the above arrangement, a plasma etching process for the wafer W and an end point detection for the plasma process are performed following the same procedures as described in Example 5. In this embodiment, the transparent member 350 for transmitting plasma emission is formed such that the end face 351a of the fitting portion 351 is leveled with the inner surface 201b of the side wall 201a as mentioned earlier. Consequently, it is possible to perform a predetermined plasma etching process for the wafer W without influencing the state of a plasma which is generated to perform the plasma etching process.

As shown in FIG. 36, the transparent member 350 is not formed in the middle of the side wall 201a of the process chamber 201. However, since the optical axis of plasma emission passes at right angles through the end wall 351b of the fitting portion 351 of the transparent member 350, the transparent member 350 does not bring about refraction or the like of the plasma emission. For this reason, the plasma emission can be detected accurately, and so the end point detection for a plasma process can be performed with a high accuracy. This improves the degree of freedom in the location of the transparent member 350 or the end point detection apparatus 362, facilitating the design of the whole plasma process system or the layout of individual components.

During the plasma etching process, on the other hand, the end wall 351b is heated to, e.g., 200° C. by the heaters 355 in order to prevent adhesion of the reaction products to the end face 351a of the fitting portion 351 of the transparent member 350. This heat is also conducted to the O-ring 345 provided between the locking portion 352 of the transparent member 350 and the side wall 201a of the process chamber 201. However, the heaters 355 heating the end wall 351b are located at the end of the fitting portion 351 projecting from the locking portion 352. Therefore, the distance from the heaters 355 to the locking portion 352 in contact with the O-ring 345 is set large by side walls 351c and 351d of the fitting portion 351 forming the projecting portion. Since quartz glass as the material of the transparent member 350 has a low thermal conductivity, these side walls 351c and 351d act as heat-insulating walls to largely suppress the conduction of heat to the O-ring 345. As an example, even if the temperature of the end wall 351b itself is 200° C., the temperature of the locking portion 352 can be decreased to about 100° C. For this reason, the temperature of the O-ring 345 does not increase greatly, and no thermal deformation takes place. Also, the O-ring 345 is improved in durability. Therefore, even when the heaters 355 heat the transparent member 350, the airtightness of the side wall 201a of the process chamber 201 is not degraded; i.e., the airtightness in the process chamber 201 is well maintained. This makes it possible to perform a predetermined plasma etching process.

In this embodiment, the fitting portion 351 of the transparent member 350 protrudes at right angles from the locking portion 352. However, as in FIG. 37, it is also possible to use a transparent member 373 in which a fitting portion 372 projects at a predetermined angle from a locking portion 371 so that an end wall 375a faces a substantially central portion of the process space S. In this case, the transparent member 373 can be mounted closer to the end of the side wall 201a. In addition, the accuracy of the end point detection of a plasma process remains unchanged from that in the case of the transparent member 350 in this embodiment. Also, the use of the transparent member 373 with this arrangement further facilitates the design of the whole plasma process system and the layout of individual components. Moreover, the present invention is applied to a plasma etching system in this embodiment. However, the present invention is also applicable to other plasma process systems, such as an ashing system and a CVD system.

As has been discussed above, in the end point detection method of this embodiment, the end point of a plasma process can be detected accurately without influencing the state of a plasma generated in a process chamber, resulting in an improved yield. Additionally, the degree of freedom in the mounting location of a transparent member is increased, and the degree of freedom in the design of a plasma process system is also increased.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. An end point detection method comprising the steps of:

sequentially detecting, when a process using a plasma is performed for an object to be processed, emission spectra in two specific wavelength bands of two active species in the plasma by using a photodetecting means;

obtaining an average value of emission intensities for each of the emission spectra during a time period;

making two graphs, each showing the relationship between said average value and time, substantially equal to each other in inclination;

calculating a ratio or a difference between the two graphs to obtain a coefficient;

obtaining a calculated value using the coefficient and a newly obtained emission intensity; and determining a point at which said calculated value exceeds a reference value as an end point of the process.

2. A method according to claim 1, wherein the specific wavelength band of said active species are set in regions in which an emission intensity of said active species appears more strongly than peak values of emission intensities of other active species.

3. A method according to claim 1, wherein said active species are selected from the group consisting of components of a process gas and reaction products formed by the plasma process.

4. A method according to claim 1, wherein the specific wavelength bands of said active species are set in regions not including a peak value of an emission intensity of silicon.

5. A method according to claim 1, wherein the process using a plasma is etching.

6. An end point detection method comprising the steps of:

sequentially detecting, when a process using a plasma is performed for an object to be processed, an emission spectrum in a specific wavelength band of at least one first active species and a peak value of an emission intensity of at least one second active species in the plasma by using photodetecting means;

obtaining an average value of an emission intensity of the emission spectrum during a time period;

making two graphs, each showing the relationship between said average value and time and the relationship between said peak value and time, substantially equal to each other in inclination;

calculating a ratio or a difference between the peak value of the emission intensity and said average value to obtain a coefficient;

obtaining a calculated value using the coefficient and a newly obtained emission intensity; and determining a point at which the calculated value exceeds a reference value as an end point of the process.

7. A method according to claim 6, wherein the specific wavelength band of said first active species or the peak value of the emission intensity of said second active species is set in a region in which an emission intensity of said first or second active species appears more strongly than peak values of emission intensities of other active species.

8. A method according to claim 6, wherein said first or second active species is selected from the group consisting of components of a process gas and reaction products formed by the plasma process.

9. A method according to claim 6, wherein the specific wavelength band of said first active species and the peak value of the emission intensity of said second active species are set in a region not including a peak value of an emission intensity of silicon.

10. A method according to claim 6, wherein a peak value of an emission intensity of carbon monoxide is used as the peak value of said second active species.

11. A method according to claim 6, wherein the process using a plasma is etching.

12. An end point detection apparatus comprising:

an average value calculating means for calculating average values of emission intensities of emission spectra obtained by detecting, by using photodetecting means, the emission spectra generated in two specific wavelength bands when a process using a plasma is performed for an object to be processed;

calculating means for calculating a ratio or a difference between average values, to obtain a calculated value;

means for making two graphs, each showing a relationship between said average value and time, made substantially equal to each other in inclination; and determining means for determining a point at which the calculated value exceeds a reference value as an end point of the process.

13. A plasma process apparatus for applying a process using a plasma to an object, comprising:

a pair of electrodes arranged in a process chamber, an object to be processed being placed on one of said electrodes, and a high frequency power being applied therebetween to convert a process gas into a plasma;

light-condensing means for condensing light emitted from the plasma in said process chamber;

photodetecting means for detecting emission spectra in two specific wavelength bands from the light condensed by said light-condensing means;

average value calculating means for calculating average values of emission intensities for each of the emission spectra on the basis of information from said photodetecting means;

calculating means for calculating a ratio or a difference between average values, to obtain a calculated value;

means for making two graphs, each showing a relationship between said average value and time, made substantially equal to each other in inclination; and determining means for determining a point at which the calculated value exceeds a reference value as an end point of the process.

14. A system according to claim 13, wherein the process using a plasma is etching.

* * * * *